United States Patent
Rougon et al.

(10) Patent No.: US 7,417,025 B2
(45) Date of Patent: Aug. 26, 2008

(54) USE OF POLY-α2,8-SIALIC ACID MIMETIC PEPTIDES TO MODULATE NCAM FUNCTIONS

(75) Inventors: Geneviève Rougon, Marseilles (FR); Pascal Torregrossa, Marseilles (FR); Melitta Schachner, Hamburg (DE); Claus Schafer Nielsen, Humlebaek (DK)

(73) Assignees: Centre National de la Recherche Scientifique, Paris (FR); Universite de la Mediterranee AIX-Marseille, Marseilles (FR); Schafer-N, Copenhagen (DK); Universitaetsklinikum Hamburg-Eppendorf, Hamburg (DE)

( * ) Notice: Subject to any disclaimer, the term of this patent is extended or adjusted under 35 U.S.C. 154(b) by 48 days.

(21) Appl. No.: 10/531,701

(22) PCT Filed: Oct. 16, 2003

(86) PCT No.: PCT/IB03/05108

§ 371 (c)(1),
(2), (4) Date: Dec. 13, 2005

(87) PCT Pub. No.: WO2004/035609

PCT Pub. Date: Apr. 29, 2004

(65) Prior Publication Data

US 2006/0122108 A1    Jun. 8, 2006

(30) Foreign Application Priority Data

Oct. 16, 2002    (EP) .................................. 02292548

(51) Int. Cl.
| A61K 38/10 | (2006.01) |
| A61K 38/12 | (2006.01) |
| A61K 38/16 | (2006.01) |
| C07K 5/12  | (2006.01) |
| C07K 7/00  | (2006.01) |
| C07K 7/08  | (2006.01) |
| C07K 7/64  | (2006.01) |
| C07K 14/00 | (2006.01) |

(52) U.S. Cl. ................ 514/11; 514/2; 514/13; 514/14; 530/300; 530/317; 530/325; 530/327; 530/333

(58) Field of Classification Search ............ None
See application file for complete search history.

(56) References Cited

U.S. PATENT DOCUMENTS 6,346,512 B1 *   2/2002   Blaschuk et al. .............. 514/11

FOREIGN PATENT DOCUMENTS

| WO | 98/08874  | 3/1998 |
| WO | 00/54805  | 9/2000 |
| WO | 02/46408  | 6/2002 |

OTHER PUBLICATIONS

Rao Y, Wu X-F, Gariepy J, Rutishauser U, Siu C-H, Identification of a Peptide Sequence Invovled in Homophilic Binding in the Neural Cell Adhesion Molecule NCAM, Journal of Cell Biology, 1992, 118(4): 937-949.*

Storms SD, Rutishauser U, A Role of Polysialic Acid in Neural Cell Adhesion Molecule Heterophilic Binding to Proteoglycans, Journal of Biological Chemistry, 1998, 273(4): 27124-27129.*

J. S. Shin et al.: "Monoclonal Antibodies Specific for *Neisseria meningitidis* Group B Polysaccharide and Their Peptide Mimotopes" Infection and Immunity, American Society for Microbiology, vol. 69, No. 5, p. 3335-3342, May 2001. XP-002228383.

Christian M. Hurpin et al.: "Bactericidal Activity of Two IgG2a Murine Monoclonal Antibodies with Distinct Fine Specificities for Group B *Neisseria meningitidis* Capsular Polysaccharide" Hybridoma, vol. 11, No. 6, p. 677-687, 1992. XP009004404.

* cited by examiner

Primary Examiner—Anish Gupta
Assistant Examiner—Julie Ha
(74) Attorney, Agent, or Firm—Oblon, Spivak, McClelland, Maier & Neustadt, P.C.

(57) ABSTRACT

The invention relates to the use of a peptide consisting of 5 to 30 amino acid residues, preferably 9 to 15, most preferably about 12 amino acid residues, said peptide comprising a B epitope of a poly-α2,8 sialic acid attached to NCAM, which is recognized by an anti-poly-α2,8 sialic acid (PSA) antibody, for the preparation of a medicament for modulating NCAM functions, to be administered for the prevention and/or the treatment of neurodegenerative diseases, brain and spine lesions, age-related learning and memory problems, and cancer.

4 Claims, 12 Drawing Sheets

SEQUENCE LISTING

<160> NUMBER OF SEQ ID NOS: 32

<210> SEQ ID NO 1

```
<211> LENGTH: 12
<212> TYPE: PRT
<213> ORGANISM: Artificial
<220> FEATURE:
<223> OTHER INFORMATION: Synthetic Peptide

<400> SEQUENCE: 1

Asp Ser Pro Leu Val Pro Phe Ile Asp Phe His Pro
1               5                   10

<210> SEQ ID NO 2
<211> LENGTH: 12
<212> TYPE: PRT
<213> ORGANISM: Artificial
<220> FEATURE:
<223> OTHER INFORMATION: Synthetic Peptide

<400> SEQUENCE: 2

Leu Trp Gln Pro Pro Leu Ile Pro Gly Ile Asp Phe
1               5                   10

<210> SEQ ID NO 3
<211> LENGTH: 12
<212> TYPE: PRT
<213> ORGANISM: Artificial
<220> FEATURE:
<223> OTHER INFORMATION: Synthetic Peptide

<400> SEQUENCE: 3

Gln Ile Glu Pro Trp Phe Thr Pro Glu Asp Phe Pro
1               5                   10

<210> SEQ ID NO 4
<211> LENGTH: 12
<212> TYPE: PRT
<213> ORGANISM: Artificial
<220> FEATURE:
<223> OTHER INFORMATION: Synthetic Peptide

<400> SEQUENCE: 4

Thr Arg Leu Ala Pro Leu Val Phe Pro Leu Asp Tyr
1               5                   10

<210> SEQ ID NO 5
<211> LENGTH: 12
<212> TYPE: PRT
<213> ORGANISM: Artificial
<220> FEATURE:
<223> OTHER INFORMATION: Synthetic Peptide

<400> SEQUENCE: 5

Ser Trp Leu Gln Met Pro Trp Ala Leu Val Arg Thr
1               5                   10

<210> SEQ ID NO 6
<211> LENGTH: 12
<212> TYPE: PRT
<213> ORGANISM: Artificial
<220> FEATURE:
<223> OTHER INFORMATION: Synthetic Peptide

<400> SEQUENCE: 6

Glu Ile His Leu Arg Met Ile Lys Gln Ile Thr Ile
1               5                   10

<210> SEQ ID NO 7
<211> LENGTH: 12
```

```
<212> TYPE: PRT
<213> ORGANISM: Artificial
<220> FEATURE:
<223> OTHER INFORMATION: Synthetic Peptide

<400> SEQUENCE: 7

Trp His Leu Glu Tyr Met Trp Arg Trp Pro Arg Leu
1               5                   10

<210> SEQ ID NO 8
<211> LENGTH: 12
<212> TYPE: PRT
<213> ORGANISM: Artificial
<220> FEATURE:
<223> OTHER INFORMATION: Synthetic Peptide

<400> SEQUENCE: 8

Leu Ile Glu Gln Arg Leu Pro Lys His Ile Leu Thr
1               5                   10

<210> SEQ ID NO 9
<211> LENGTH: 12
<212> TYPE: PRT
<213> ORGANISM: Artificial
<220> FEATURE:
<223> OTHER INFORMATION: Synthetic Peptide

<400> SEQUENCE: 9

Tyr Glu Thr Ser Ser Ser Arg Leu Leu Ala Tyr Ala
1               5                   10

<210> SEQ ID NO 10
<211> LENGTH: 12
<212> TYPE: PRT
<213> ORGANISM: Artificial
<220> FEATURE:
<223> OTHER INFORMATION: Synthetic Peptide

<400> SEQUENCE: 10

Thr Leu Ala Ser Gln Leu Ser Asn Thr Ser Ala Tyr
1               5                   10

<210> SEQ ID NO 11
<211> LENGTH: 12
<212> TYPE: PRT
<213> ORGANISM: Artificial
<220> FEATURE:
<223> OTHER INFORMATION: Synthetic Peptide

<400> SEQUENCE: 11

Ser Asp Gln Gly Val Asn Gly Ser Trp Ser Asn Pro
1               5                   10

<210> SEQ ID NO 12
<211> LENGTH: 13
<212> TYPE: PRT
<213> ORGANISM: Artificial
<220> FEATURE:
<223> OTHER INFORMATION: Synthetic Peptide

<400> SEQUENCE: 12

Trp His Asn Trp Asn Leu Trp Ala Pro Ala Ser Pro Thr
1               5                   10

<210> SEQ ID NO 13
<211> LENGTH: 12
<212> TYPE: PRT
```

```
<213> ORGANISM: Artificial
<220> FEATURE:
<223> OTHER INFORMATION: Synthetic Peptide

<400> SEQUENCE: 13

Trp His Trp Gln Trp Thr Pro Trp Ser Ile Gln Pro
1               5                   10

<210> SEQ ID NO 14
<211> LENGTH: 12
<212> TYPE: PRT
<213> ORGANISM: Artificial
<220> FEATURE:
<223> OTHER INFORMATION: Synthetic Peptide

<400> SEQUENCE: 14

Ile Lys Ser Pro Leu Thr Trp Leu Val Pro Pro Asp
1               5                   10

<210> SEQ ID NO 15
<211> LENGTH: 12
<212> TYPE: PRT
<213> ORGANISM: Artificial
<220> FEATURE:
<223> OTHER INFORMATION: Synthetic Peptide

<400> SEQUENCE: 15

Ser His Leu Asp Leu Ser Thr Gly His Arg Thr Ser
1               5                   10

<210> SEQ ID NO 16
<211> LENGTH: 12
<212> TYPE: PRT
<213> ORGANISM: Artificial
<220> FEATURE:
<223> OTHER INFORMATION: Synthetic Peptide

<400> SEQUENCE: 16

Cys Tyr Pro Leu Asn Pro Glu Val Tyr His Cys Gly
1               5                   10

<210> SEQ ID NO 17
<211> LENGTH: 12
<212> TYPE: PRT
<213> ORGANISM: Artificial
<220> FEATURE:
<223> OTHER INFORMATION: Synthetic Peptide

<400> SEQUENCE: 17

Cys Trp Pro Leu Ser His Ser Val Ile Val Cys Gly
1               5                   10

<210> SEQ ID NO 18
<211> LENGTH: 12
<212> TYPE: PRT
<213> ORGANISM: Artificial
<220> FEATURE:
<223> OTHER INFORMATION: Synthetic Peptide

<400> SEQUENCE: 18

Cys Ser Ser Val Thr Ala Trp Thr Thr Gly Cys Gly
1               5                   10

<210> SEQ ID NO 19
<211> LENGTH: 11
<212> TYPE: PRT
<213> ORGANISM: Artificial
```

```
<220> FEATURE:
<223> OTHER INFORMATION: Synthetic Peptide

<400> SEQUENCE: 19

Cys Tyr Met Ala Ser Gly Val Phe Leu Cys Gly
1               5                   10

<210> SEQ ID NO 20
<211> LENGTH: 12
<212> TYPE: PRT
<213> ORGANISM: Artificial
<220> FEATURE:
<223> OTHER INFORMATION: Synthetic Peptide

<400> SEQUENCE: 20

Cys Trp Pro Leu Gly Pro Ser Thr Tyr Ile Cys Gly
1               5                   10

<210> SEQ ID NO 21
<211> LENGTH: 12
<212> TYPE: PRT
<213> ORGANISM: Artificial
<220> FEATURE:
<223> OTHER INFORMATION: Synthetic Peptide

<400> SEQUENCE: 21

Cys Ser Leu Ile Ala Ser Met Glu Thr Gly Cys Gly
1               5                   10

<210> SEQ ID NO 22
<211> LENGTH: 12
<212> TYPE: PRT
<213> ORGANISM: Artificial
<220> FEATURE:
<223> OTHER INFORMATION: Synthetic Peptide

<400> SEQUENCE: 22

Cys Ser Lys Ile Ala Ser Met Glu Thr Gly Cys Gly
1               5                   10

<210> SEQ ID NO 23
<211> LENGTH: 12
<212> TYPE: PRT
<213> ORGANISM: Artificial
<220> FEATURE:
<223> OTHER INFORMATION: Synthetic Peptide

<400> SEQUENCE: 23

Cys Tyr Ile Gly Asp Pro Pro Phe Asn Pro Cys Gly
1               5                   10

<210> SEQ ID NO 24
<211> LENGTH: 12
<212> TYPE: PRT
<213> ORGANISM: Artificial
<220> FEATURE:
<223> OTHER INFORMATION: Synthetic Peptide

<400> SEQUENCE: 24

Cys Trp Pro Leu Gly Asp Ser Thr Val Ile Cys Gly
1               5                   10

<210> SEQ ID NO 25
<211> LENGTH: 12
<212> TYPE: PRT
<213> ORGANISM: Artificial
<220> FEATURE:
```

```
<223> OTHER INFORMATION: Synthetic Peptide

<400> SEQUENCE: 25

Cys Pro Leu Arg Leu Ala Phe Thr Phe Gly Cys Gly
1               5                   10

<210> SEQ ID NO 26
<211> LENGTH: 12
<212> TYPE: PRT
<213> ORGANISM: Artificial
<220> FEATURE:
<223> OTHER INFORMATION: Synthetic Peptide

<400> SEQUENCE: 26

Cys Thr Arg Met Ser His Gly Tyr Trp Ile Cys Gly
1               5                   10

<210> SEQ ID NO 27
<211> LENGTH: 20
<212> TYPE: DNA
<213> ORGANISM: Artificial
<220> FEATURE:
<223> OTHER INFORMATION: Synthetic DNA

<400> SEQUENCE: 27
ccctcatagt tagcgtaacg                                                   20

<210> SEQ ID NO 28
<211> LENGTH: 12
<212> TYPE: PRT
<213> ORGANISM: Artificial
<220> FEATURE:
<223> OTHER INFORMATION: Synthetic Peptide

<400> SEQUENCE: 28

Pro Asp His Ile Phe Val Phe Ser Pro Asp Leu Pro
1               5                   10

<210> SEQ ID NO 29
<211> LENGTH: 13
<212> TYPE: PRT
<213> ORGANISM: Artificial
<220> FEATURE:
<223> OTHER INFORMATION: Synthetic Peptide

<400> SEQUENCE: 29

Asp Ser Pro Leu Val Pro Phe Ile Asp Phe His Pro Cys
1               5                   10

<210> SEQ ID NO 30
<211> LENGTH: 13
<212> TYPE: PRT
<213> ORGANISM: Artificial
<220> FEATURE:
<223> OTHER INFORMATION: Synthetic Peptide

<400> SEQUENCE: 30

Pro Asp His Ile Phe Val Phe Ser Pro Asp Leu Pro Cys
1               5                   10

<210> SEQ ID NO 31
<211> LENGTH: 7
<212> TYPE: PRT
<213> ORGANISM: Artificial
<220> FEATURE:
<223> OTHER INFORMATION: Synthetic Peptide
```

```
<400> SEQUENCE: 31

Asp His Gln Arg Phe Phe Val
1               5

<210> SEQ ID NO 32
<211> LENGTH: 7
<212> TYPE: PRT
<213> ORGANISM: Artificial
<220> FEATURE:
<223> OTHER INFORMATION: Synthetic Peptide

<400> SEQUENCE: 32

Ala His Gln Ala Ser Phe Val
1               5
```

USE OF POLY-α2,8-SIALIC ACID MIMETIC PEPTIDES TO MODULATE NCAM FUNCTIONS

The invention relates to the use of poly-α2,8-sialic acid (PSA) mimetic peptides to modulate specifically PSA-dependent NCAM functions in vitro and in vivo, and to their application for the treatment of neurodegenerative diseases, brain and spine lesions, age-related learning and memory problems, and cancer.

The ability of cell to modify its cell surface interactions with other cells, including neurons and glial cells, is a critical component of nervous tissue development, remodelling and repair, as well as tumor formation and metastasis. Among many candidate molecules that are potentially involved in such a process, isoforms of the neural cell adhesion molecule (NCAM), a member of the IgG super-family, carrying an unconventional carbohydrate polymer, poly-α2,8-sialic acid (PSA), are of particular interest.

PSA is a polymer of negatively charged N-acetyl-neuraminic acid (sialic acid) residues in an alpha 2,8 linkage. Single PSA chain carried by NCAM, consists generally of at least 30 repeating units with the chain length varying substantially in NCAM isolated from various sources (von Der Ohe et al., Glycobiology, 2002, 12, 47-63; Rougon et al., Eur. J. Cell. Biol., 1993a, 61, 197-207). By comparison, poly-α2,8-sialic acid which is found in the capsule of bacteria such as *Neisseria meningitidis* Group B and *E. coli* K1 forms longer polymers of about 200 repeating units. Studies using NMR microscopy indicate that PSA has a helical structure in solution consisting of eight or more contiguous sialic acid units (Rougon et al., 1993a, precited; Yamasaki et al. 1991). PSA has a large hydrated volume and high negative charge density, and therefore is well placed to attenuate adhesion forces and to negatively regulate overall cell surface interactions (Rutishauser et al., Science, 1988, 240, 53-57). All the known alternatively spliced isoforms of NCAM can be polysialized at the fifth Ig-like domain (Rougon et al., 1993 a, precited) and NCAM is the only clearly identified carrier of polysialic acid in the nervous system (Rougon et al., J. Cell. Biol., 1986, 103, 2429-2437). Although, there is one report describing the association of PSA with the α chain of the Na channel (Zuber et al J. Biol. Chem., 1992, 267, 9965-9971), the absence of PSA immunoreactivity in NCAM knock-out mice (Cremer et al., Nature, 1994, 367, 455457) suggests that NCAM is the major if not the only carrier of PSA in vertebrate brain.

The attachment of PSA to NCAM is a developmentally regulated process; NCAM with high PSA content is associated with morphogenetic changes during development such as cell migration, synaptogenesis and axonal growth and branching, while in adult brain poorly sialylated forms of NCAM are dominating (Rougon et al., *Polysialic Acid*, 1993b, Roth J. R., Rutishauser U. and Troy F. A. (eds), Birkhauser-Verlag: Basel, 323-333; Rutishauser et al, 1998, precited; Edelman et al., Annu. Rev. Cell. Biol., 1986, 2, 81-116). However, PSA-NCAM does persist in adult brain structures that display a high degree of plasticity (Rougon et al., 1993a, precited). For example, PSA-NCAM is required for two essential forms of activity-induced synaptic plasticity, long-term potentiation (LTP) and long-term depression (LTD), that are believed to be central to learning and memory as well as activity-dependent pattern formation during development. (Muller et al, Neuron, 1996, 17, 413-422). Indeed, hippocampal tissue prepared from the NCAM mutant mice exhibited a markedly reduced capacity for LTP as well as LTD and this defect could be mimicked by the enzymatic destruction of the PSA moiety of NCAM. These observations indicate that PSA rather than the NCAM protein is required for plasticity. Morphological plasticity occurring in the hypothalamo-neurohypophyseal system (Theodosis et al., J. Neurosci., 1999, 19, 10228-10236) is also dependent upon the presence of PSA as in vivo injection of endoneuraminidase prevents it.

PSA-NCAM is re-expressed in several pathological situations such as muscle regeneration, axonal regeneration and brain tumors (Figarella-Branger et al., Cancer Res., 1990, 50, 6364-6370; Dubois et al., Neuromuscul. Disord., 1994, 4, 171-182; Aubert et al., Comp. Neurol., 1998, 399, 1-19; Muller et al., Neuroscience, 1994, 61, 441-445) or brain neurodegenerative diseases (Le Gal La Salle et al., J. Neurosci., 1992, 12, 872-882). Based on these observations, PSA-NCAM emerged as an important permissive factor for dynamic changes in cell surface interactions required for morphogenesis and tissue remodelling (Rougon et al., 1993b, precited; Figarella-Branger, 1993; Rutishauser, Development, 1992, 99-104).

Many tumors with neural and endocrine characteristics expressed PSA-NCAM. For example, PSA-NCAM had been detected in neuroblastomas and medulloblastomas (Figarella-Branger et al., precited), small cell carcinoma of the lung (Patel et al., Int. J. Cancer, 1989, 44, 573-578) and rhabdomyosarcomas, and is possibly related to the invasive and metastatic potential of these tumors (Rougon et al., 1993b, precited). Recently, injection of neuraminidase into a nude mouse model for metastasis showed that removal of PSA on the primary tumor delayed metastasis. (Daniel et al, Oncogene, 2001, 20, 997-1004).

Thus, the molecule PSA-NCAM and more precisely the carbohydrate PSA represents one of the potential targets of future therapeutic approaches to promote plasticity and functional recovery after brain damage or to prevent metastasis formation.

Therefore, several strategies have been developed to modulate PSA functions:

genetic manipulations: NCAM or polylsialyltransferase knock-out mice (Cremer et al., precited): this strategy does not open perspective for therapy, enzymatic digestion: endoneuraminidase (Theodosis et al., precited; Daniel et al., precited): its therapeutic potential is rather limited owing to its large size and restricted diffusion in vivo and to the possibility of inducing an immune response, anti-PSA monoclonal antibodies (Monnier et al., Developmental Biology, 2001, 229, 1-14); their therapeutic potential is rather limited owing to their antibody nature, Colominic acid, a PSA analog isolated from bacterial capsule; its therapeutic potential is rather limited owing to its instability at acidic pH and to the impossibility to control its exact composition in terms of purity and homogeneity (calibration of the sialic acid chain length, from one batch to another), N-butanoylmannosamine (ManBut), a small molecule capable of inhibiting PSA biosynthesis in vitro (Mahal et al., Science, 2001, 294, 380-382); its activity has not been demonstrated in vivo.

However, to date these strategies which have been used to uncover mechanisms of action or functions of PSA, have not led to the discovery of new drugs able to modulate PSA functions in vivo.

Therefore, there is a need for new molecules able to modulate specifically PSA-dependent NCAM functions in vivo, which can be used as pharmaceutical compositions for promoting plasticity and functional recovery after brain or spine damage or for preventing metastasis.

Peptides representing molecular mimetics of carbohydrate epitopes from microorganisms including *Neisseria meningitidis* group B PSA-specific epitopes have been described in view of developing safe and efficient vaccine candidate against these microorganisms (Shin et al., Infection and Immunity, 2001, 69, 3335-3342); the *Neisseria meningitidis* group B PSA-specific peptides disclosed in Shin et al., represent epitopes which are different from vertebrate cells (neurons) PSA epitopes and thus do not induce antibodies which bind to said neuronal PSA (PSA attached to NCAM) and may cause neurological damage. In addition, Shin et al. disclose only two peptides (DHQRFFV (SEQ ID NO: 31) and AHQASFV (SEQ ID NO: 32) representing mimetics of PSA-attached to NCAM epitopes, which are used as control to demonstrate the specificity of *Neisseria meningitidis* group B PSA mimetic peptides.

The inventors have isolated other peptides which are molecular mimetics of PSA-attached to NCAM epitopes and they have demonstrated that these PSA mimetic peptides are able to modulate (enhance or inhibit), in vivo, in a PSA-dependent manner, cellular processes that are normally affected by polysialylation of NCAM. For example, the inventors have demonstrated a significant effect of the PSA mimetic peptides, in vivo, on axons growth, guidance and fasciculation as well as on neurons migration. Moreover, the administration of the PSA mimetic peptides results in functional recovery after spinal cord injury and is also accompanied by reduced reactive gliosis at the site of the lesion.

In the context of the invention, poly-α2,8 sialic acid or PSA means PSA-attached to NCAM, as opposed to other PSA such as PSA from bacteria capsules.

These PSA mimetic peptides which are active in vivo at low doses (μM concentration) and do not exhibit any cytotoxicity are useful for:
the treatment of neurodegenerative diseases (Parkinson, Huntington's chorea, Alzheimer, multiple sclerosis): they are useful as adjuvants for cell therapy; graft of neuronal progenitors (expressing PSA) in combination with PSA mimetic peptides would enhance significantly progenitors migration and axon outgrowth in the damaged areas of the brain,
the treatment of brain and spine lesion: they would promote functional recovery after brain or spine damage by increasing axon survival and regeneration,
the prevention and treatment of age-related learning and memory problems: they would promote nervous system plasticity by increasing neurogenesis and/or synaptic plasticity,
the treatment of cancer: they would prevent metastasis formation by inhibiting cell migration from PSA expressing tumors, for example neuroectodermic tumors.

In addition to said therapeutic use, the PSA mimetic peptides are useful as complementary tools to uncover mechanisms of action and unknown functions of the carbohydrate PSA.

The present invention relates to the use of a peptide consisting of 5 to 30 amino acid residues, preferably 9 to 15, most preferably about 12 amino acid residues, said peptide comprising a B epitope of a poly-α2,8 sialic acid attached to NCAM, which is recognized by an anti-poly-α2,8 sialic acid antibody, for the preparation of a medicament for modulating NCAM functions.

The "B epitope recognized by an anti-PSA antibody" refers to a peptide which reacts specifically and selectively, in vitro and in vivo, with the paratope of an antibody produced by lymphoid cells in response to a stimulation with poly-α2,8 sialic acid as an immunogen. Anti-PSA antibodies prepared by standard techniques, following protocols as described for example in *Antibodies: A Laboratory Manual*, E. Howell and D Lane, Cold Spring Harbor Laboratory, 1988 are well-known in the art; they include, without limitation, monoclonal antibodies 735 (Frosch et al., P.N.A.S; 1985, 82, 1194-1198), 30H12 (Coquillat et al., Infect. Immun., 2001, 69, 7130-7139) or MenB (ABCYS AbC0019; Rougon et al., J. Cell. Biol., 1986, 103, 2429-2437).

The invention includes the use of linear and cyclic peptides. Preferred cyclic peptides as defined in the invention comprise peptides in which the side chain of one amino acid in the peptide chain is attached covalently to the side chain of another amino acid in the peptide chain via formation of a covalent bond, such as a disulfide bond between two cysteine residues.

The peptides as defined in the invention refer to peptides which have the following activities:
antibody binding activity: they are recognized specifically by an anti-PSA monoclonal or polyclonal antibody, and
biological activity: they have the activity of modulating (enhancing or inhibiting) PSA-dependent NCAM functions.

The peptides as defined in the invention are denominated hereafter PSA mimetic peptides, mimetic peptides or peptides. Unless otherwise specified, said peptides are either linear or cyclic.

The mimetic peptides antibody-binding activity is verified by standard immunoassay which are well-known by a person skilled in the art; for example, 100% peptide binding is observed at concentrations of $10^{-4}$M and above in an ELISA with an anti-PSA monoclonal antibody at the concentration of 2.5 μg/well, and this antibody binding activity is specifically inhibited by a PSA analog such as colominic acid.

The mimetic peptides biological activity is verified by standard cell growth and cell migration assays in vitro or in vivo, which are well-known by a person skilled in the art; for example, assays on primary neurons from different sources (dorsal root ganglion, cerebellar neurons, retina, . . . ) show the following effects:
a significant dose dependent increase of neurite length in vivo and in vitro,
a significant effect on axonal guidance in vivo and in vitro (axons defasciculation), and
a significant increase or inhibition of cell migration.

In addition, functional assays including study of the functional recovery from spinal cord hemisection by well-known tests (BBB test: Basso, Beattie and Bresnahan test; Basso et al., Restor. Neurol. Neurosci, 2002, 5, 189-218; rotarod test) show a significant locomotor and fine motor coordination recovery in the mimetic peptide treated animals, by comparison with the animals treated with a non relevant peptide.

The mimetic peptide biological activity is specifically inhibited by enzymatic digestion with endoneuraminidase and is absent in NCAM knock-out mice.

According to an advantageous embodiment of the use of the invention, said peptide comprises a sequence which is selected from the group consisting of the sequences SEQ ID NO: 1 to 12 and 14 to 26, corresponding respectively to DSPLVPFIDFHP, LWQPPLIPGIDF, QIEPWFTPEDFP, TRLAPLVFPLDY, SWLQMPWALVRT, EIHLRMIKQITI, WHLEYMWRWPRL, LIEQRLPKHILT, YETSSSRL-LAYA, TLASQLSNTSAY, SDQGVNGSWSNP, WHNWN-LWAPASPT, IKSPLTWLVPPD, SHLDLSTGHRTS, CYPLNPEVYHCG, CWPLSHSVIVCG, CSSVTAWT-TGCG, CYMASGVFLCG, CWPLGPSTYICG, CSLIAS- METGCG, CSKIASMETGCG, CYIGDPPFNPCG, CWPLGDSTVICG CPLRLAFTFGCG and CTRMSHGY-WICG.

According to another advantageous embodiment of the use of the invention, said peptide is a linear peptide comprising the sequence WHWQWTPWSIQP (SEQ ID NO: 13).

According to another advantageous embodiment of the use of the invention, said peptide is a cyclic peptide comprising the sequence WHWQWTPWSIQP (SEQ ID NO: 13).

The invention also includes the use of any functional derivative of the peptides as defined above, comprising one or more modifications which do not affect substantially the antibody binding and biological activities of the initial peptide.

Such modifications include for example: addition and/or deletion and/or substitution of one or more amino acid residue in the peptide chain, and/or replacement of one or more of the amide bond by a non-amide bond, and/or replacement of one or more amino acid side chain by a different chemical moiety, and/or protection of the N-terminus, the C-terminus, or one or more of the side chain by a protecting group, and/or introduction of double bonds and/or cyclization and/or stereo-specificity into the amino acid chain to increase rigidity, and/or binding affinity and/or enhance resistance to enzymatic degradation of the peptides. Since all the variations are known in the art, it is submitted that a person skilled in the art will be able to produce, test, identify and select other peptides/epitopes according to the present invention.

For instance, it is possible to substitute amino acids by equivalent amino acids. "Equivalent amino acid" is used herein to name any amino acid that may substitutes for one of the amino acids belonging to the initial peptide structure without modifying the antibody binding and biological activities of the initial peptide structure. These equivalent amino acids may be determined by their structural homology with the initial amino acids to be replaced and by their biological activity on the target cells of the peptides according to the invention. As an illustrative example, it should be mentioned the possibility of carrying out substitutions like, for example, leucine by valine or isoleucine, aspartic acid by glutamic acid, glutamine by asparagine, asparagine by lysine etc., it being understood that the reverse substitutions are permitted in the same conditions. In some cases, it may also be possible to replace of a residue in the L-form by a residue in the D-form or the replacement of the glutamine (Q) residue by a pyro-glutamic acid compound.

Preferably, said peptide consists of a sequence selected from the group consisting of SEQ ID NO: 1 to SEQ ID NO: 26.

Most preferably, said peptide is selected from the group consisting of:

- a linear peptide presenting SEQ ID NO: 1 (DSPLVPFIDFHP) denominated hereafter p21, and
- a cyclic peptide in which the side chain of the cysteine residue at position 1 of SEQ ID NO: 18 (CSSVTAWTTGCG) or SEQ ID NO: 22 (CSKIASMETGCG) is attached covalently to the side chain residue of the cysteine at position 11 of SEQ ID NO: 18 or SEQ ID NO: 22 via a disulfide bond; said peptides are denominated hereafter, respectively p65 and p66.

According to another advantageous embodiment of the use of the invention, said peptide is associated with another peptide or non-peptide molecule and/or incorporated into a suitable support including for example, polymers, lipidic vesicles, microspheres, proteins and the like. Preferably, the other peptide or nonpeptide molecule and/or the support as defined above enables the mimetic peptide to cross the brain-blood barrier.

Such association which may improve the peptide solubility, absorption, bioavailability, biological half life, is formed, by using techniques well known in the art; it may be through, without limitation, covalent bonding (e.g., amide bond, disulfide bond . . . ), or through chelation, electrostatic interactions, hydrophobic interactions, hydrogen bonding, ion-dipole interactions, dipole-dipole interactions, or any combination of the above.

According to another advantageous embodiment of the use of the invention, said peptide is incorporated in a complex comprising a plurality of identical or different peptides according to the invention, linked by covalent or non-covalent bonds.

According to another advantageous embodiment of the use of the invention, said peptide is associated with a marker such as a fluorescent marker, to facilitate the detection of the peptides according to the invention.

According to another advantageous embodiment of the invention, said peptide is included in a fusion protein to allow expression of said peptide.

According to another advantageous embodiment of the use of the invention, said medicament is for the prevention and/or the treatment of a pathological condition selected from the group consisting of: neurodegenerative diseases, brain and spine lesions, age-related learning and memory problems.

According to another advantageous embodiment of the use of the invention, a peptide selected from the group consisting of: the linear and the cyclic peptides comprising or consisting of the sequences SEQ ID NO: 1 to 12 and 14 to 26 and the cyclic peptides comprising SEQ ID NO: 13, or a complex thereof as defined above, is used for the preparation of a medicament for the prevention and/or the treatment of cancer.

The peptides as defined in the present invention may be prepared by any suitable process. Preferably, it is obtained by chemical synthesis in liquid or solid phase by successive couplings of the different amino acid residues to be incorporated (from the N-terminal end to the C-terminal end in liquid phase, or from the C-terminal end to the N-terminal end in solid phase) wherein the N-terminal ends and the reactive side chains are previously blocked by conventional groups. For solid phase synthesis the technique described by Merrifield (J. Am. Chem. Soc., 1964, 85, 2149-2154) may be used.

The peptides as defined in the present invention may also be obtained by genetic engineering technology. A typical example comprise culturing a host cell containing an expression vector comprising a nucleic acid sequence encoding said peptide, under conditions suitable for the expression of the peptide, and recovering the peptide from the host cell culture. The peptide may be included in a fusion protein by cloning a cDNA into an expression vector in frame with a polynucleotide coding for the peptide of the invention. Alternatively, multimer of identical or different peptides can also be produced by expressing a polynucleotide coding for multiple copies of a monomer, or coding for different monomers.

The invention further concerns a medicament comprising a peptide or a peptide complex as defined above, with the exclusion of the linear peptide comprising the sequence SEQ ID NO: 13.

The invention further concerns a pharmaceutical composition comprising an effective amount of a peptide or a peptide complex as defined above, with the exclusion of the linear peptide comprising the sequence SEQ ID NO:13, in a combination with a pharmaceutically acceptable carrier.

The carriers of the pharmaceutical compositions of the invention can be any vehicle for parenteral, intrathecal, oral, aerosol, nasal, or ocular administration of drugs acting on the nervous system. For example, a composition according to the invention is administered intrathecally which enables the penetration of the composition directly into the Central Nervous System. Alternatively, it is administered through the nose which enables the penetration of the aerosol composition to the Central Nervous System through the olfactory nerve, or via the ocular route, or by any other suitable method of administration as described in W. M. Pardridge, *Peptide drug Delivery*, Raven Press, N.Y., 1991.

The amount of peptide in the composition is in a concentration ranges from about 0.1 µM to about 10 µM. The preferred frequency of administration and effective dosage will vary from one subject to another.

The invention also concerns a peptide as defined above, consisting of 5 to 30 amino acid residues, preferably 9 to 15, most preferably about 12 amino acid residues, said peptide comprising a B epitope of a poly-α2,8 sialic acid attached to NCAM, which is recognized by an anti-poly-α2,8 sialic acid (PSA) antibody, with the exclusion of the linear peptides comprising the sequences selected in the group consisting of: WHWQWTPWSIQP (SEQ ID NO: 13); DHQRFFV (SEQ ID NO: 31) and AHQASFV (SEQ ID NO: 32).

The invention also provides a polynucleotide encoding said peptide according to the invention, as well as the complement of said polynucleotide, and fragments of at least 5 nucleotides thereof.

In particular, the invention provides the nucleotide sequences encoding the peptides SEQ ID NO: 1 to 12 and SEQ ID NO: 14 to 26, including all possible examples of nucleotide sequences encoding these peptides which result from the degeneration of the genetic code.

Nucleic acids of the invention may be obtained by the well-known methods of recombinant DNA technology and/or chemical DNA synthesis.

The invention also provides recombinant vectors comprising a polynucleotide encoding a peptide of the invention. Vectors of the invention are preferably expression vectors, wherein a sequence encoding a peptide of the invention is placed under control of appropriate transcriptional and translational control elements. These vectors may be obtained and introduced in a host cell by the well-known recombinant DNA and genetic engineering techniques.

The invention also comprises a prokaryotic or eukaryotic host cell transformed by a vector of the invention, preferably an expression vector.

The peptides as defined in the invention have the following advantages:
 they are active in vivo at low doses (0.5 µM concentration),
 they are stable in vivo,
 they are very efficient in vivo since they act extracellularly; thus, their activity is not limited by their ability to penetrate inside the cell,
 they are not toxic, and
 they can be produced easily in large quantities.

The present invention will be further illustrated by the additional description and drawings which follow, which refer to examples illustrating the isolation, the binding specificity and the biological effects of the PSA mimetic peptides according to the invention. It should be understood however that these examples are given only by way of illustration of the invention and do not constitute in anyway a limitation thereof.

(G) quantification of the effect of the mimetic peptides on the mean length of the longest neurite. *** $P<0.001$ compared with control with Student's t test. (H) cumulative frequency distribution plot of the mean length of the longest neurite.

Figure 3:
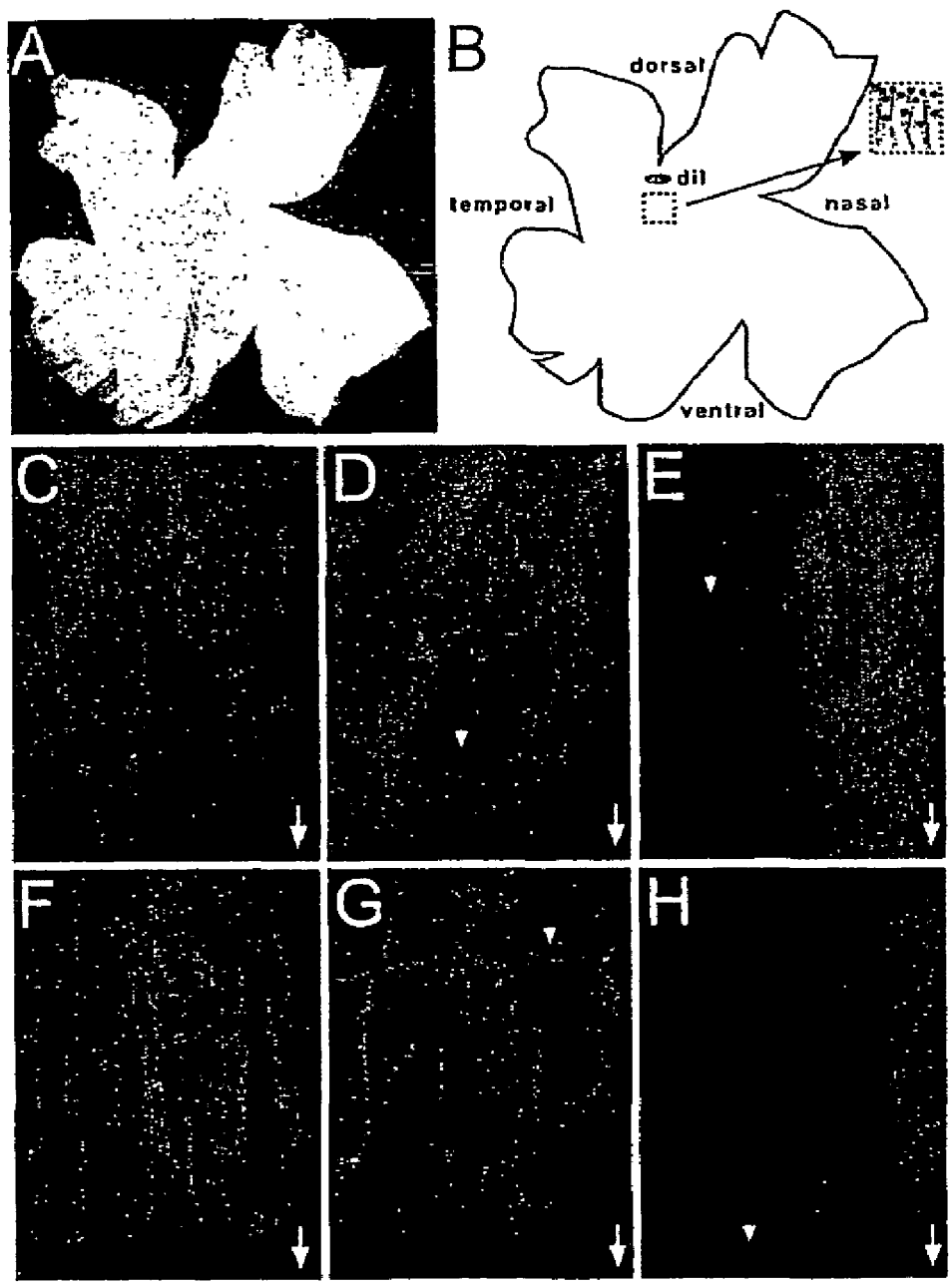

FIG. 3 illustrates the effect of PSA mimetic peptide p65 on fasciculation and guidance in vivo: E9 chick whole retina mounted preparation (A) and its schematic drawing demonstrating the position of the DiI crystal (B). The dashed rectangle indicates the area from which photographs were taken. Arrows point toward the optic fissure. Axons of E9 chick retina injected at E3 with the reverse peptide (C,F) or the p65 peptide (D,G,E,H). Arrowheads show examples of axons that leave their fascicle and run perpendicularly to it.

Figure 4:
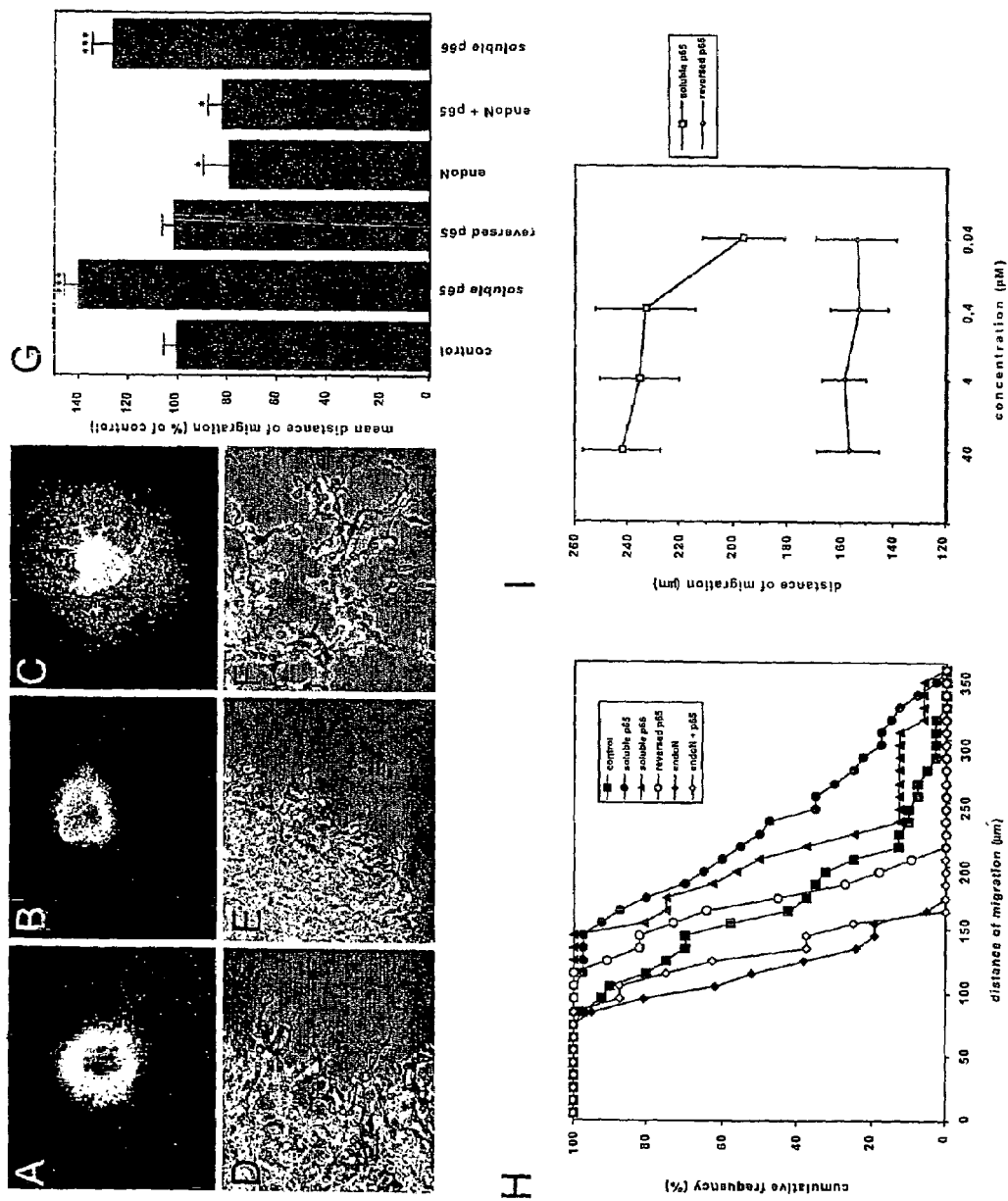
Figure 5:
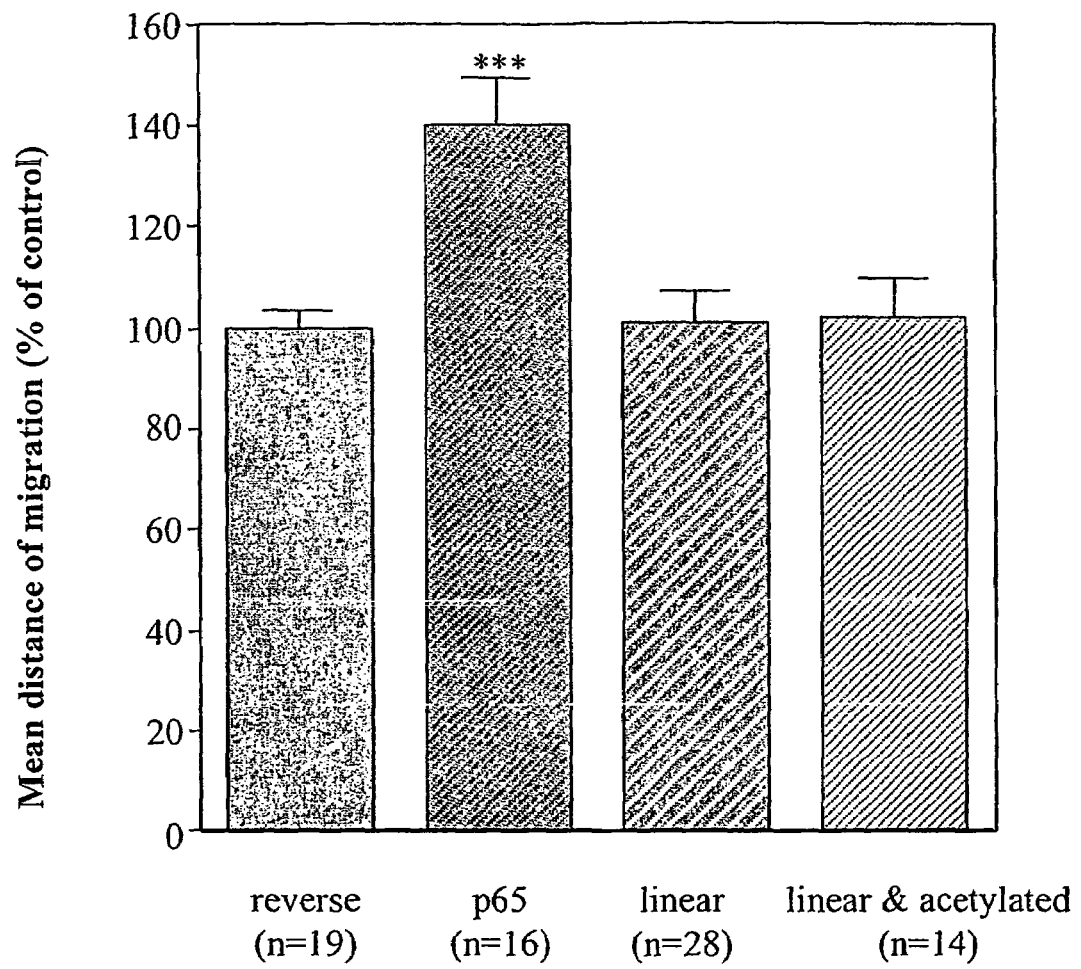
Figure 6:
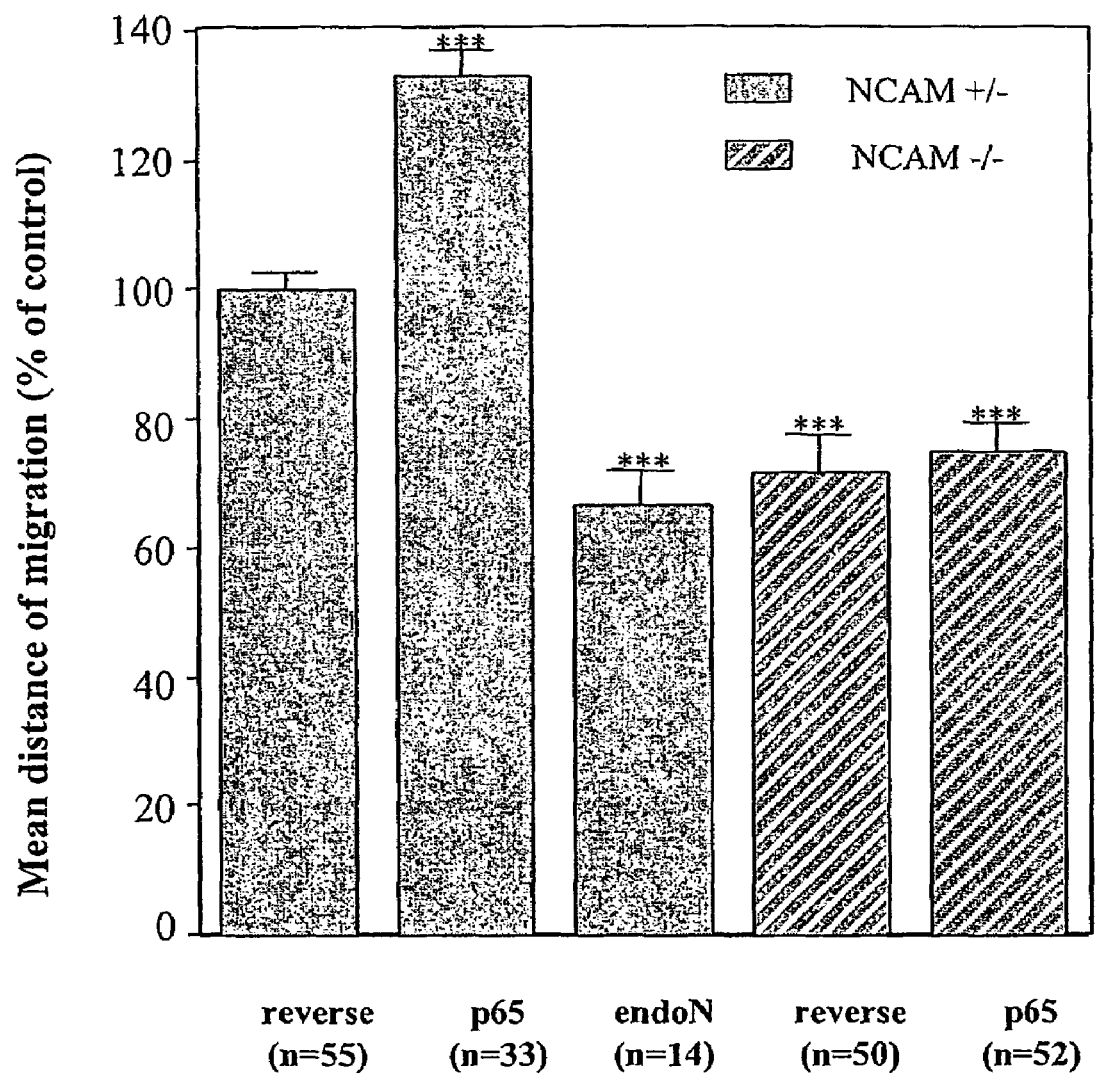
Figure 7:
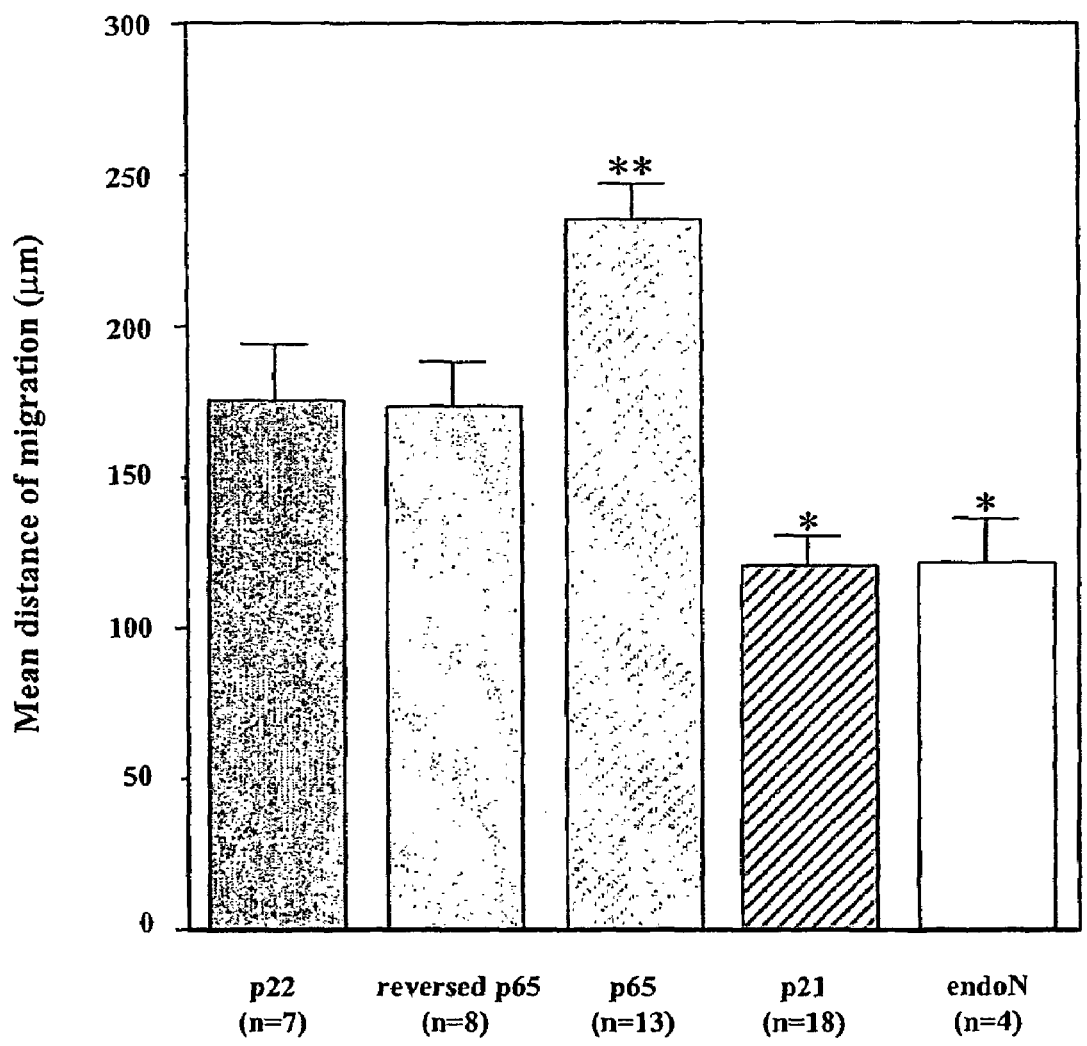

FIGS. 4 to 7 illustrate the effect of PSA mimetic peptides on cell migration in vitro, analysed on subventricular zone explants (P1) from normal mice (NCAM +/+), heterozygous mice (NCAM +/−) or knock-out mice (NCAM −/−), cultured in presence of the mimetic peptides (p65, p21, p66), different form of said peptides (cyclic, linear, linear and acetylated), the control peptides (reverse p65 and reverse p66 and p22) or endosialidase N:

FIG. 4 illustrates the effect of the reverse p65 peptide (A,D), endosialidase N (B,E) or the mimetic peptides p65 and p66 (C,F). (G) quantification of the effect of the mimetic peptides on the cell migration mean distance. * $P<0.001$ compared with control with student's t test. (H) cumulative frequency distribution plot of the mean distance of migration. (I) Dose-dependant effect of the p65 peptide on the mean distance of cell migration, FIG. 5 illustrates the effect of different forms of p65 mimetic peptide (cyclic, linear, linear and acetylated) on the cell migration mean distance, compared with reverse p65 control peptide. * $P<0.001$ compared with control with student's t test, FIG. 6 illustrates the effect of p65 mimetic peptide on the cell migration mean distance in knock-out mice (SCAM −/−) or heterozygous mice (NCAM +/−). Endo N treated cells from NCAM +/−mice and reverse p65 treated cells are included for comparison. * $P<0.001$ compared with control with student's t test, and FIG. 7 illustrates the effect of p65 and p21 mimetic peptides on the cell migration mean distance. Endo N treated cells and cells treated with control peptides (reverse p65 and p22) are included for comparison. * $P<0.001$ compared with control with student's t test.

Figure 8:
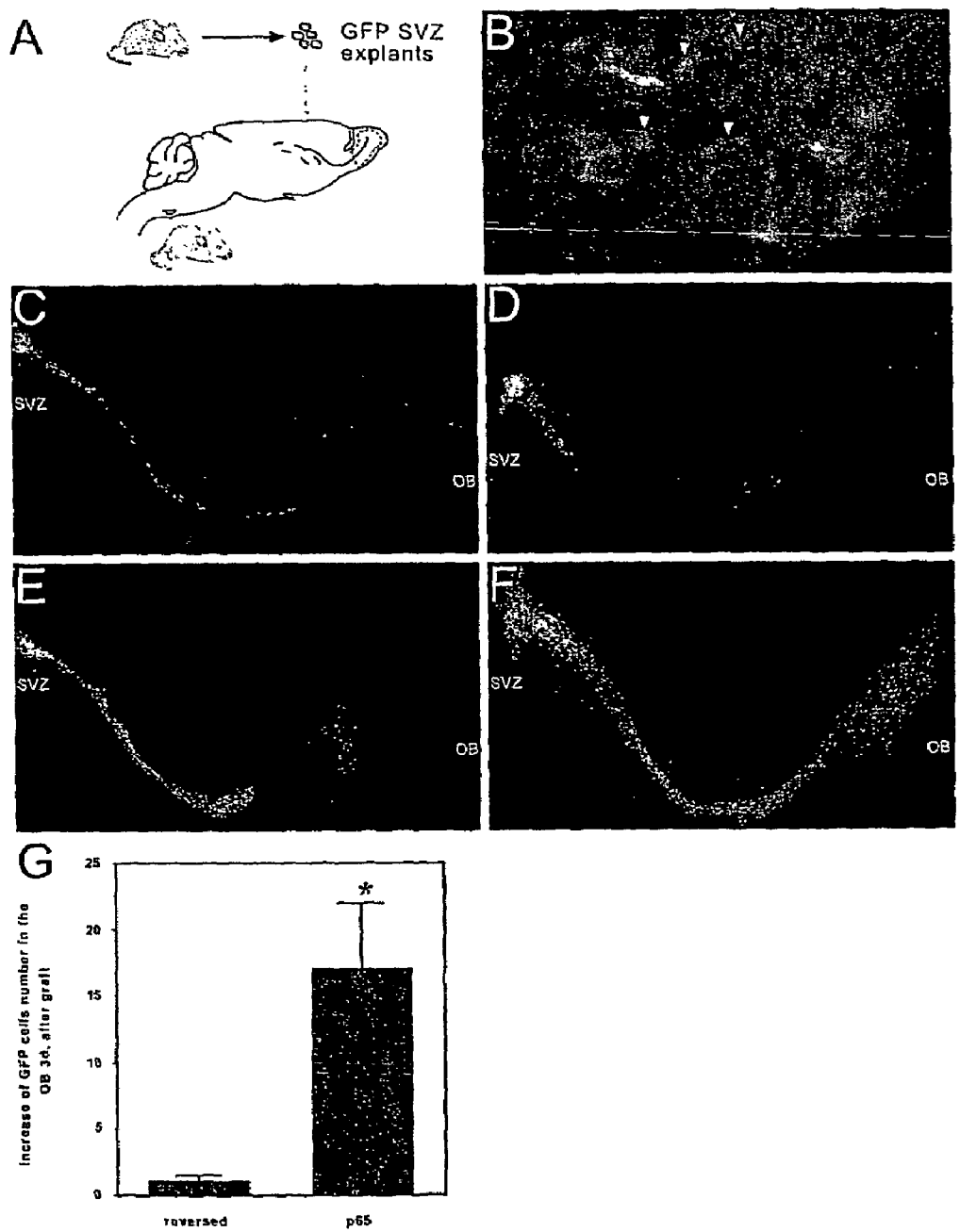

FIG. 8 illustrates the effect of PSA mimetic peptide p65 on cell migration in vivo: (A) schematic drawing of the transplantation. (B) Confocal microscopy photography of a section showing the RMS (Rostral Migration Stream) of grafted mice in presence of p65 peptide. Arrowheads show examples of GFP and PSA positive cells. SVZ explants (P1) were grafted in presence of the reverse peptide (C,D) or the p65 peptide (E,F) and brains were analysed three days after graft (C,E) or four day after graft (D,F). (G) quantification of the effect of the p65 peptide on the number of GFP positive cells that reach the olfactory bulb three days after graft. * $P<0.05$ compared with control with Student's t test.

Figure 9:
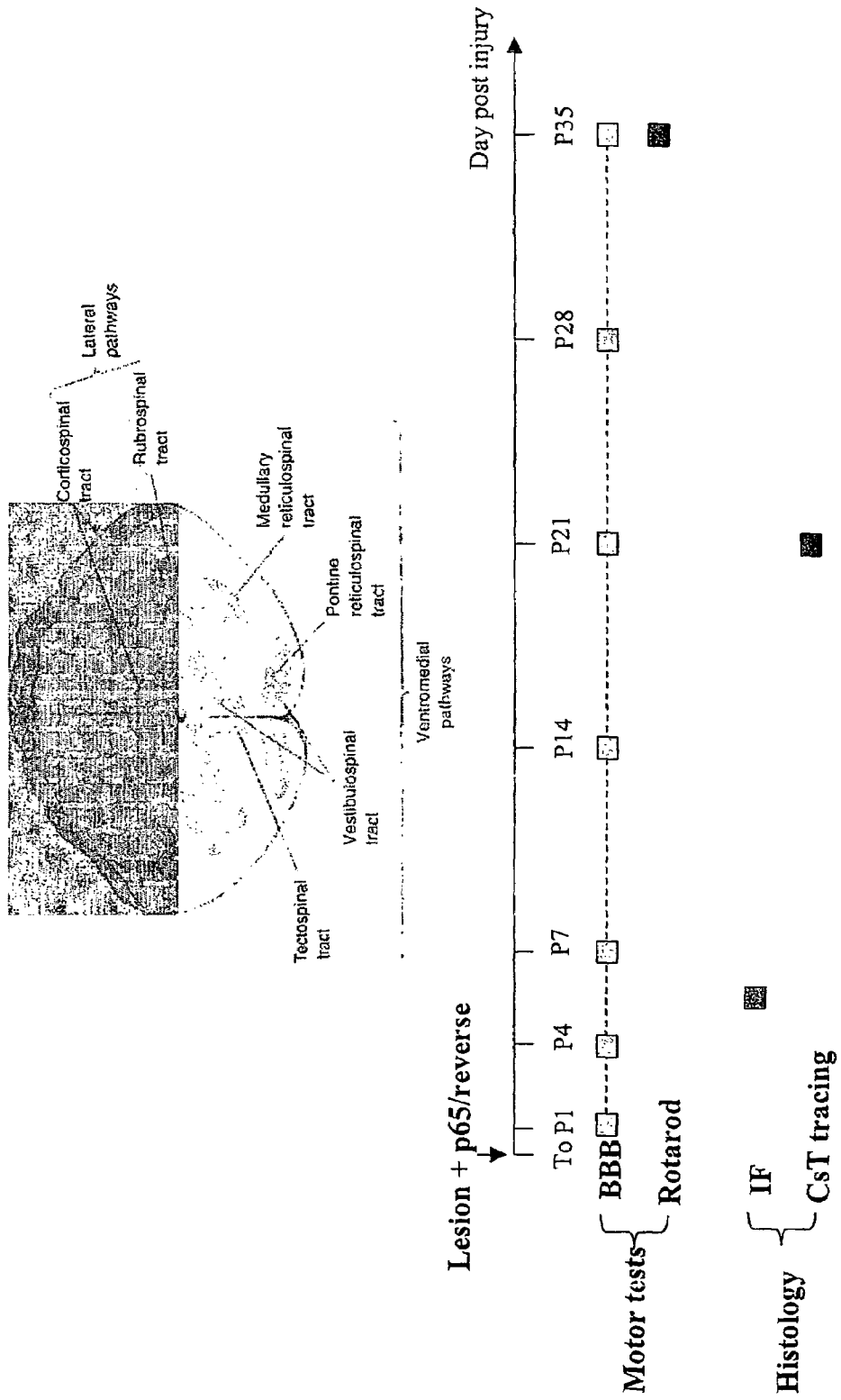

FIG. 9 illustrates the protocol used to analyze the functional recovery from spinal cord injury after injection of p65 peptide or p65 reverse peptide taken as control.

Figure 10:
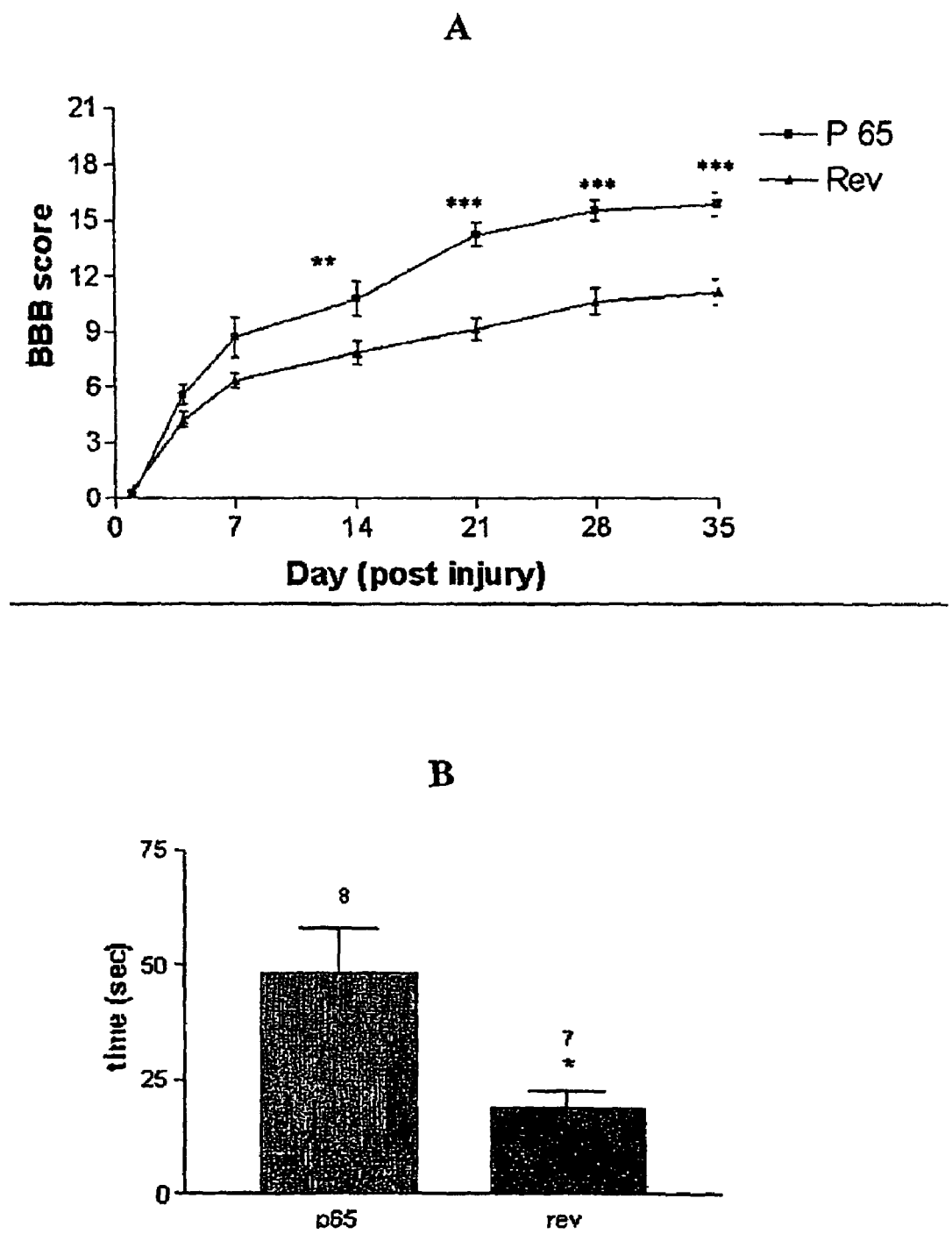

FIG. 10 illustrates the functional recovery from spinal cord injury after injection of p65 peptide (p65) or p65 reverse peptide (Rev) taken as control. A: Basso, Beattie and Bresnahan test (BBB test). B: Rotarod test n=11 for p65 and n=8 for Rev. * $P<0.01$,  $P<0.01$, * $P<0.05$, compared with control with Student's t test.

Figure 11:
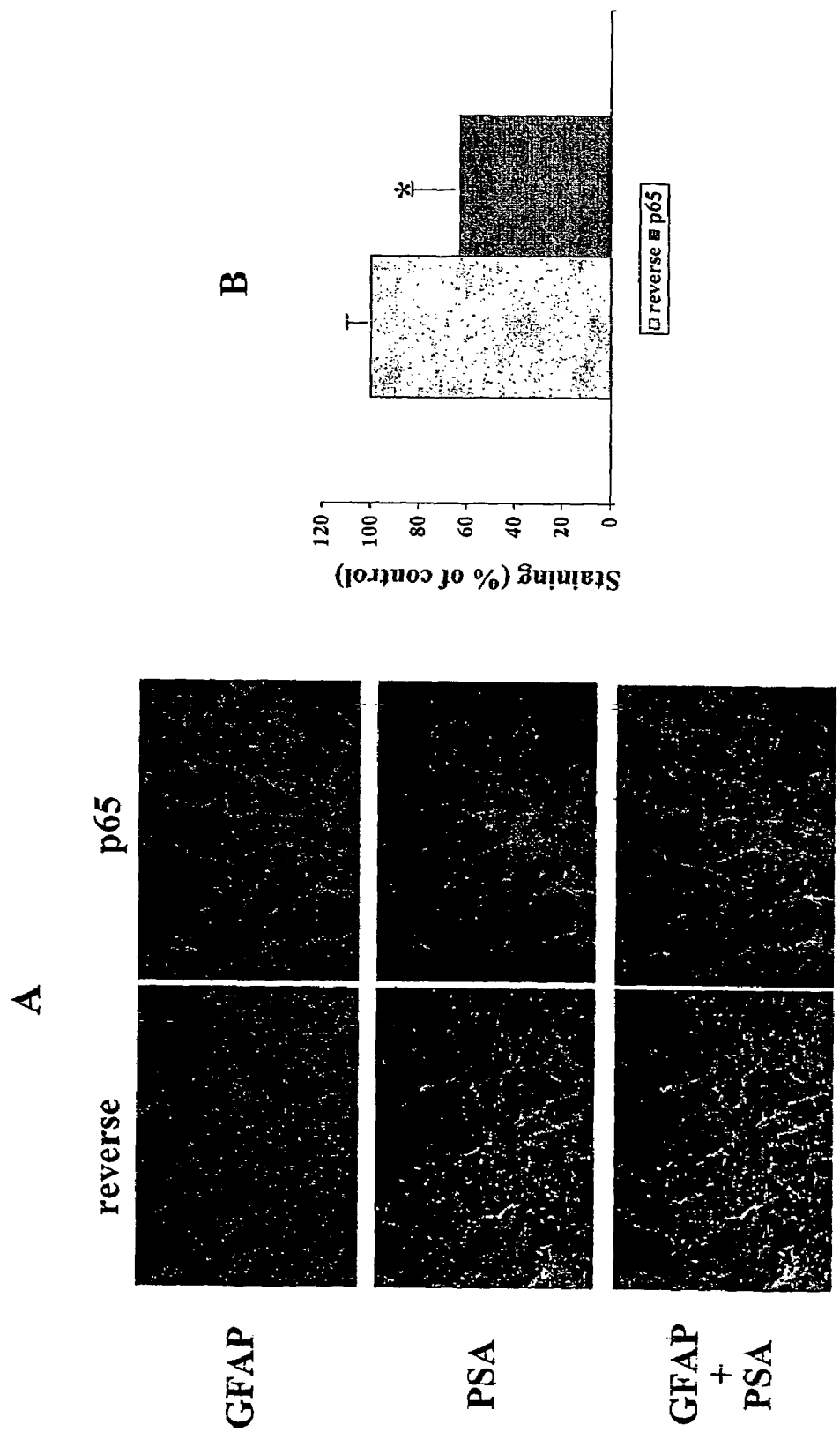

FIG. 11 illustrates the decrease of reactive gliosis after spinal cord injury, in mice treated with p65 peptide or p65 reverse peptide taken as control. A: Immunofluorescence analysis using anti-GFAP and anti-PSA antibodies alone or in combination (double-labelling). B: quantification of the GFAP staining. * P<0.05, compared with control with Student's t test.

Figure 12:
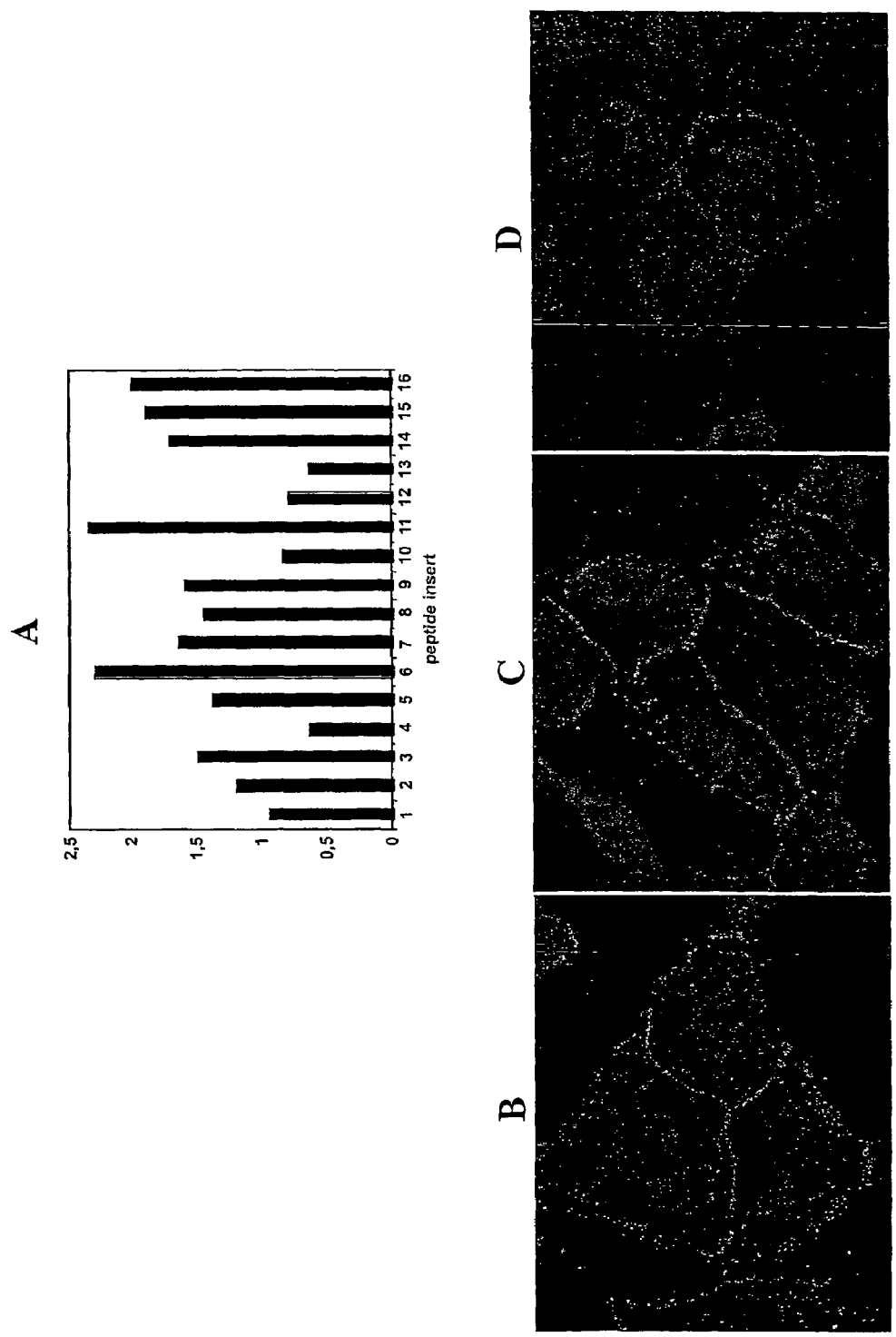

FIG. 12 illustrates the binding specificity of the cyclic mimetic peptides:

FIG. 12A: ELISA using 30H12 anti-PSA monoclonal antibody-coated plates. Numbers 1 to 16 correspond to the peptide sequences as presented in Table IV.

FIGS. 12B, 12C and 12D: competitive binding to PSA-NCAM expressing cells. B: pre-incubation of p65 (1 mM) or p66 (1 mM) with MenB anti-PSA antibody. C: 30H12 anti-PSA antibody without peptide. D: pre-incubation of p65 (1 mM) or p66 (1 mM) with 30H12 anti-PSA antibody.

EXAMPLE 1

Peptide Library Screening with Anti-PSA Monoclonal Antibody

1) Materials and Methods
   1.1) Materials

Peptide 12-mer Phage Display Library

Two libraries were screened. The first library (12™ Phage Display peptide Library, NEW ENGLAND BIOLABS) comprises 12-mer linear peptides presented on the surface of M13-like phage particles as fusion protein to the N-terminus of the pIII minor coat-protein (5 copies/phage particle). The variance of the library differs from $10^8$ to $10^9$ peptides with constant sequence length.

The second library, prepared as described in Felici et al. (J. Mol. Biol., 1991, 222, 301-301), comprises 12-mer cyclic peptides including 2 cysteine residues at position 1 and 11 linked by a disulfide bond, presented on the surface of M13-like phage particles as fusion protein to the N-terminus of the pVIII major coat-protein (100 copies/phage). The library comprises approximately $10^8$ peptides with constant sequence length.

Anti-PSA Monoclonal Antibody (mAb).

Anti-PSA monoclonal antibodies, prepared by standard techniques as described in Antibodies: *A Laboratory Manual*, E. Howell and D Lane, Cold Spring Harbor Laboratory, 1988, are used. For example, monoclonal antibodies 735 (Frosch et al., P.N.A.S; 1985, 82, 1194-1198), 30H12 (IgG 2a; Coquillat et al., Infect. Immun., 2001, 69, 7130-7139) or MenB (IgM; ABCYS AbC0019) may be used.

plates (Maxisorp™ NUNC)
   tubes (Maxisorp™, NUNC)
   *E. coli* strain ER2537 (NEW ENGLAND BIOLABS)
   96 gIII sequencing primer (NEW ENGLAND BIOLABS):
   5'CCCTCATAGTTAGCGTAACG-3' (SEQ ID NO: 27)
   1.2) Buffers
   Blocking solution: 0.5% BSA in PBS
   Coating solution: 25 µg/ml anti-PSA mAb in PBS
   TBS: 50 mM Tris-HCl pH 8.6, 150 mM NaCl.
   TBST: TBS containing 0.1% or 0.5% Tween 20.
   PEG /NaCl: 20% (W/V) polyethylene glycol-8000, 2.5 M NaCl.
   Iodide Buffer: 10 mM Tris-HCl, pH 8.0, 1 mM EDTA, 4M NaCl.

1.3) Method

Maxisorp™ tubes were incubated overnight with 2 ml of coating solution, at +4° C., with gentle agitation, according to the manual of the Ph.D. 12™ Phage Display peptide Library kit (NEW ENGLAND BIOLABS). The coating solution was removed and used for the coating of new tubes for new rounds of biopanning. The coated tubes were incubated with 2 ml of blocking solution for 1 h and washed 6 times with TBST. The tubes were filled with 2 ml of phage solution (7.5 $10^{10}$ pfu/ml in TBST containing 0.1% Tween 20) and incubated with gentle agitation at room temperature for 1 h. After removal of the phage solution, the tubes were washed 10 times with TBST. Bound phages were either eluted, specifically with 1 mM colominic acid in TBS for 1 h, or non-specifically with 0.2 M glycine HCl (pH 2.2) for 10 min with immediate neutralization with 1 M Tris-HCl. Eluates were amplified in 20 ml of *E. coli* ER2537 culture (starting $OD_{600}$: 0.03), for 4.5 h at 37° C. with vigorous shaking. The cultures were centrifuged for 10 min at 10,000 rpm at 4° C. The supernatant was transferred to a fresh tube and centrifuged for another 10 minutes. PEG/NaCl solution was added to the supernatant (1 volume PEG/NaCl for 6 volumes supernatant) and phage was precipitated overnight at 4° C. The solution containing the precipitate was centrifuged for 15 min at 10,000 rpm at 4° C. The supernatant was decanted and the pellet was suspended in 1 ml TBS and re-precipitated with ⅙ volume of PEG/NaCl for 1 h on ice. After centrifugation, the pellet was finally suspended in 200 ml TBS, 0.02% $NaN_3$.

This amplified eluate was dissolved in TBST and a second and a third round of biopanning were carried out as described above; for the second round, the TBST used for washing and phage incubation contained 0.1% Tween 20; in the third round the content was 0.5%.

The non-amplified eluate from the third round was subsequently tittered on LB/IPTG/X-gal plates. Blue plaques were picked and the phage clone amplified in 2 ml *E. coli* ER2537 culture for 4.5 h at 37° C., with vigorous shaking. After centrifugation for 10 min at 10,000 rpm, at 4° C., the supernatant was mixed with ⅙ volume PEG/NaCl and the phage precipitated at 4° C. overnight. The precipitate was centrifuged for 15 min at 10,000 rpm at 4° C. The pellet was suspended in 100 µl TBS. 10 µl from this solution were mixed with 100 µl iodide buffer and 250 µl ethanol for the precipitation of the single-stranded phage DNA. After incubation for 10 min at room temperature, the solution was centrifuged for 10 min at 15,000 rpm. The supernatant was discarded and the pellet washed in 70% ethanol and dried briefly under vacuum. The pellet was suspended in 10 µl distilled water containing the sequencing primer for automated sequencing of the peptide insert (BigDye Terminator byte sequencing with standard M13-40 primer on an Applied Biosystem 877/377). The remaining single phage solution was used for ELISA experiments.

2) Results

After three rounds of biopanning, phages presenting the following sequences were isolated (Table I, II, III and IV).

TABLE I

Linear peptides sequences isolated from 17 different phages eluted with in 1 mM colominic acid

| SEQ ID NO: | sequence |
|---|---|
| 5 | SWLQMPWALVRT |
| 5 | SWLQMPWALVRT |
| 4 | TRLAPLVFPLDY |
| 6 | EIHLRMIKQITI |
| 7 | WHLEYMWRWPRL |
| 5 | SWLQMPWALVRT |
| 5 | SWLQMPWALVRT |
| 8 | LIEQRLPKHILT |
| 9 | YETSSSRLLAYA |
| 5 | SWLQMPWALVRT |
| 10 | TLASQLSNTSAY |
| 5 | SWLQMPWALVRT |
| 11 | SDQGVNGSWSNP |
| 4 | TRLAPLVFPLDY |
| 5 | TRLAPLVFPLDY |
| 5 | SWLQMPWALVRT |
| 4 | TRLAPLVFPLDY |

TABLE II

Linear peptides sequences isolated from 20 different phages eluted with 0.2 M glycine.

| SEQ ID NO: | Sequence |
|---|---|
| 1 | DSPLVPFIDFHP |
| 2 | LWQPPLLIPGIDF |
| 2 | LWQPPLLIPGIDF |
| 12 | WHNWNLWAPASPT |
| 3 | QIEPWFTPEDFP |
| 1 | DSPLVPFIDFHP |
| 3 | QIEPWFTPEDFP |
| 13 | WHWQWTPWSIQP |
| 2 | LWQPPLIPGIDF |
| 5 | SWLQMPWALVRT |
| 2 | LWQPPLIPGIDF |
| 1 | DSPLVPFIDFHP |
| 15 | SHLDLSTGHRTS |
| 1 | DSPLVPFIDFHP |
| 1 | DSPLVPFIDFHP |

TABLE II-continued

Linear peptides sequences isolated from 20 different phages eluted with 0.2 M glycine.

| SEQ ID NO: | Sequence |
|---|---|
| 5 | SWLQMPWALVRT |
| 1 | DSPLVPFIDFHP |
| 14 | IKSPLTWLVPPD |
| 1 | DSPLVPFIDFHP |
| 1 | DSPLVPFIDFHP |

5 linear peptides have a high occurrence in the phages isolated after three rounds of biopanning (Table III).

TABLE III

Alignment of the 5 more frequent linear sequences

| Frequence | SEQ ID NO: | Sequence | | | | | | | | | | |
|---|---|---|---|---|---|---|---|---|---|---|---|---|
| 9/40 | 5 | S | W | L | Q | M | P | W | A | L | V | R | T |
| 8/40 | 1 | D | S | P | L | V | P | F | I | D | F | H | P |
| 4/40 | 4 | T | R | L | A | P | L | V | F | P | L | D | Y |
| 4/40 | 2 | L | W | Q | P | P | L | I | I | G | I | D | F |
| 2/40 | 3 | Q | I | E | P | W | F | T | P | E | D | F | P |

An alignment at GeneStream Align Home page to sequence SEQ ID NO: 1, showed that the sequence similarity varies from 42.9% for SEQ ID NO: 2, 30.8% for SEQ ID NO: 3, 28.6% for SEQ ID NO: 4, to 8.3% for SEQ ID NO: 5.

34 phage clones displaying cyclic peptides bound the antibody in a dose dependent manner after three cycles of biopanning, and they did not bind to an irrelevant antiboty of the same isotype. DNA from 16 of these clones showing the highest value in the ELISA test were prepared and sequenced (Table IV). 3 clones exhibited the same sequence (SEQ ID NO: 17) and the dimeric motif WP was found in 5 clones.

TABLE IV

Cyclic peptides sequences isolated from phages

| SEQ ID NO: | Peptide n° | Sequence |
|---|---|---|
| SEQ ID NO: 16 | 2 | CYPLNPEVYHCG |
| SEQ ID NO: 17 | 3 | CWPLSHSVIVCG |
| SEQ ID NO: 17 | 5 | CWPLSHSVIVCG |
| SEQ ID NO: 18 | 6 (p65) | CSSVTAWTTGCG |
| SEQ ID NO: 19 | 8 | CYMASGVFLCG |
| SEQ ID NO: 17 | 9 | CWPLSHSVIVCG |
| SEQ ID NO: 20 | 10 | CWPLGPSTYICG |
| SEQ ID NO: 21 | 11 (p66) | CSLIASMETGCG |

TABLE IV-continued

Cyclic peptides sequences isolated from phages

| SEQ ID NO: | Peptide n° | Sequence |
|---|---|---|
| SEQ ID NO: 22 | | CSKIASMETGCG |
| SEQ ID NO: 16 | 12 | CYPLNPEVYHCG |
| SEQ ID NO: 23 | 13 | CYIGDPPFNPCG |
| SEQ ID NO: 24 | 14 | CWPLGDSTVICG |
| SEQ ID NO: 25 | 15 | CPLRLAFTFGCG |
| SEQ ID NO: 26 | 16 | CTRMSHGYWICG |

EXAMPLE 2

Analysis of Peptides Specificity by Competitive Phage ELISA

1) Materials and Methods
 1.1) Materials
 anti-PSA monoclonal antibody 735 or 30H12
 MaxiSorp™ plates (NUNC) for antibody coating: ELISA plates
 microtiter plates (NUNC) for phage dilution: dilution plates
 M13 bacteriophages presenting peptides of Tables III and IV from example 1
 HRP conjugated anti-M13 antibody (PHARMACIA 27-9411-01)
 ABTS [2,2'Azino-bis(3-ethylbenzothiazoline-6-sulfonic acid), SIGMA]
 Colominic acid (SIGMA)
 Dextran (SIGMA)
 1.2) Buffers
 PBS pH 7.4
 Blocking solution: 0.5% BSA in PBS
 TBS
 TBST: TBS containing 0.05% Tween 20
 Horse Radish Peroxydase-conjugated anti-M13 antibody solution: 1/5000 in TBST
 Horse Radish Peroxydase (HRP) substrate solution: 22 mg ABTS in 100 µl 50 mM sodium citrate pH 4.0. Prior enzymatic reaction, add 36 ml 30% $H_2O_2$ to 21 ml ABTS solution.
 competitor solution: 1 mM colominic acid in TBST
 control solution: 1 mM dextran in TBST 1.3) Method
 MaxiSorp™ plate wells were coated with 100 µl mAb solution (25 µg/ml) for 2 h at room temperature. The control wells were coated only with the blocking solution. In parallel, the phage dilution plates were blocked with 200 µl blocking solution for 2 h. The antibody coated wells and the control wells of the ELISA plates were blocked with 200 µl blocking solution for 1 h. In parallel the phage dilution plates were washed 6 times with TBST and 120 µl TBST was added to the wells. An appropriate volume of a phage solution was added to the first well and the volume was adjusted to 140 µl with TBST. The phage solution in well one was diluted in the ratio 1/7 by taking 20 µl out of the first well and transferring into the second, also to achieving the total volume of 140 µl. This was repeated for the remaining wells. The phage dilutions for the control wells were done the in same way. The blocked ELISA plate was washed 6 times with TBST and the phage dilutions or the competitor solution were added. After incubation for 1 h, the plates were washed 10 times with TBST. After incubation for 1 h, the wells were washed 10 times with TBST. 100 µl of the HRP-conjugated M13 antibody solution was added to the wells. After incubation for 1 h, the wells were washed 10 times with TBST and 100 µl of the HRP substrate solution (with $H_2O_2$) was added to the wells. The plates were read at 405 nm using a microplate reader.

2) Results
 The binding specificity of peptides SEQ ID NO: 1 to 5 from example I was tested in a competitive ELISA using colominic acid as competitor. The results presented in Tables V to IX are expressed as percentage of binding, by comparison with phage presenting SEQ ID NO: 5 at a concentration of 710 ng/well (100%)

TABLEAU V

Binding of phage presenting SEQ ID NO: 5 to mAb 735

| | Phage concentration (ng/well) | | | | | | |
|---|---|---|---|---|---|---|---|
| | 710 | 109 | 18 | 3 | 1 | 0 | 0 |
| phage | 100 ± 3 | 102 ± 0 | 98 ± 0 | 73 ± 4 | 18 ± 2 | 4 ± 3 | 2 ± 1 |
| phage + colominic acid | 106 ± 0 | 103 ± 5 | 90 ± 0 | 36 ± 0 | 5 ± 0 | 1 ± 0 | 1 ± 0 |
| phage + dextran | 102 ± 2 | 103 ± 1 | 97 ± 1 | 62 ± 1 | 14 ± 0 | 5 ± 0 | 1 ± 0 |
| phage + BSA | 5 ± 1 | 3 ± 1 | 1 ± 0 | 1 ± 0 | 0 ± 0 | 0 ± 0 | 0 ± 0 |

TABLEAU VI

Binding of phage presenting SEQ ID NO: 1 to mAb 735

| | Phage concentration (ng/well) | | | | | | |
|---|---|---|---|---|---|---|---|
| | 1003 | 154 | 26 | 4 | 1 | 0 | 0 |
| phage + mAb735 | 108 ± 2 | 111 ± 7 | 111 ± 3 | 112 ± 12 | 86 ± 15 | 28 ± 2 | 7 ± 0 |
| phage + colominic acid + mAb735 | 108 ± 0 | 109 ± 12 | 90 ± 3 | 42 ± 3 | 12 ± 1 | 2 ± 1 | 0 ± 0 |
| phage + dextran + mAb735 | 109 ± 6 | 110 ± 6 | 112 ± 5 | 107 ± 1 | 77 ± 4 | 24 ± 4 | 8 ± 0 |
| phage + BSA | 10 ± 1 | 4 ± 1 | 3 ± 0 | 1 ± 1 | 0 ± 0 | 0 ± 0 | 0 ± 0 |

TABLEAU VII

Binding of phage presenting SEQ ID NO: 4 to mAb 735

| | Phage concentration (ng/well) | | | | | | |
|---|---|---|---|---|---|---|---|
| | 870 | 134 | 22 | 4 | 1 | 0 | 0 |
| phage + mAb735 | 107 ± 7 | 112 ± 10 | 109 ± 1 | 108 ± 2 | 67 ± 2 | 17 ± 0 | 4 ± 0 |
| phage + colominic acid + mAb735 | 96 ± 7 | 106 ± 3 | 89 ± 1 | 29 ± 1 | 5 ± 0 | 1 ± 0 | 0 ± 0 |
| phage + dextran + mAb735 | 96 ± 12 | 108 ± 7 | 113 ± 0 | 105 ± 0 | 66 ± 3 | 16 ± 1 | 5 ± 0 |
| phage + BSA | 10 ± 1 | 4 ± 1 | 1 ± 1 | 0 ± 0 | 0 ± 0 | 0 ± 0 | 0 ± 0 |

TABLEAU VIII

Binding of phage presenting SEQ ID NO: 2 to mAb 735

| | Phage concentration (ng/well) | | | | | | |
|---|---|---|---|---|---|---|---|
| | 796 | 122 | 20 | 3 | 1 | 0 | 0 |
| phage + mAb735 | 108 ± 5 | 109 ± 3 | 112 ± 10 | 89 ± 11 | 27 ± 4 | 4 ± 2 | 2 ± 1 |
| phage + colominic acid + mAb735 | 109 ± 6 | 114 ± 12 | 100 ± 6 | 48 ± 6 | 10 ± 1 | 1 ± 0 | 1 ± 0 |
| phage + dextran + mAb735 | 109 ± 8 | 111 ± 6 | 110 ± 5 | 99 ± 1 | 27 ± 1 | 5 ± 1 | 1 ± 0 |
| phage + BSA | 12 ± 1 | 9 ± 1 | 4 ± 3 | 2 ± 1 | 1 ± 0 | 0 ± 0 | 0 ± 0 |

TABLEAU IX

Binding of phage presenting SEQ ID NO: 3 to mAb 735

| | Phage concentration (ng/well) | | | | | | |
|---|---|---|---|---|---|---|---|
| | 859 | 132 | 22 | 4 | 1 | 0 | 0 |
| phage + mAb735 | 111 ± 8 | 109 ± 16 | 114 ± 8 | 99 ± 10 | 50 ± 1 | 13 ± 1 | 6 ± 0 |
| phage + colominic acid + mAb735 | 104 ± 2 | 107 ± 2 | 85 ± 7 | 27 ± 3 | 4 ± 1 | 1 ± 1 | 0 ± 0 |
| phage + dextran + mAb735 | 109 ± 2 | 108 ± 0 | 108 ± 3 | 107 ± 8 | 57 ± 3 | 13 ± 1 | 6 ± 0 |
| phage + BSA | 10 ± 0 | 5 ± 1 | 2 ± 1 | 1 ± 0 | 0 ± 0 | 0 ± 0 | 0 ± 0 |

The phage presenting sequence SEQ ID NO: 1 (DSPLVPFIDFHP) showed the best binding to mAb 735 in comparison with the other phages. This binding was competed with colominic acid, whereas dextran showed no competition effects. The phage presenting sequence SEQ ID NO: 4 showed similar values. Because of the low occurrence of sequence SEQ ID NO: 4 it was decided to synthesize sequence SEQ ID NO: 1 (peptide p21) and a randomized variant of sequence SEQ ID NO: 1 (peptide p22: PDHIFVFSPDLP, SEQ ID NO: 28) as control.

The phages presenting cyclic peptides corresponding to sequence CSSVTAWTTGCG (SEQ ID NO: 18) and CSKIASMETGCG (SEQ ID NO: 22) respectively, in which the two cysteine residues are linked via a disulfide-bridge, showed the best binding to mAb 30H12 in comparison with the other phages. Thus, it was decided to synthesize the corresponding cyclic peptides (p65 and p66).

EXAMPLE 3

Analysis of p21, p65 and p66 Specificity by Competitive Peptide ELISA, ELISA and Competitive Binding To Psa-Ncam Expressing Cells 1) Preparation of Biotinylated Peptide-BSA Conjugates
    1.1) Materials
    m-maleimidobenzoyl-N-hydroxysuccinimide ester (MBS, SIGMA M2786, PIERCE 1) 20311)
    biotinamidocaproate-N-hydroxysuccinimide ester (NHS-Biotin, SIGMA 02643, PIERCE 20217)
    dimethylformamide (DMF, SIGMA)
    BSA (CALBIOCHEM 122605)
    cysteine-containing synthetic peptides deriving from p21 (DSPLVPFIDFHPC, SEQ ID NO: 29), p65 and p66 and corresponding cysteine-containing control peptides deriving from p22 (PDHIFVFSPDLPC, SEQ ID NO: 30), p65 and p66 reverse peptides, respectively.
    PD-10 size exclusion column (AMERSHAM-PHARMACIA 17-0851-01)

Ultrafree-4-centrifuge filters & tub Biomax 50K NMWL membrane, 4 ml volume (MILLIPORE UFV4BQK25)
L-cysteine (SIGMA)

1.2) Buffers

MBS stock solution: 13 mg/ml in DMF
NHS-Biotin stock solution: 2.5 mg/ml in DMF (These concentrations lead to highly activated BSA molecules with approximately 5 molecules biotin/BSA molecule)
conjugation buffer: 0.083 M $NaH_2PO_4$, 0.9 M NaCl, pH 7.2.
PBS pH 7.4,
cysteine solution: L-cysteine 100 mg/ml in conjugation buffer 1.3) Method 10 mg BSA were dissolved in 2 ml conjugation buffer and 140 µl of the MBS/NHS-Biotin stock solution were added. The solution was incubated for 1 h at room temperature, with gentle agitation. The PD-10 column was equilibrated with 50 ml conjugation buffer. After adding 2.14 ml of the solution onto the column, the activated BSA was eluted with 0.5 ml aliquots of conjugation buffer. The protein elution was monitored at 280 nm. An appropriate amount of the cysteine containing peptide was dissolved in 1 ml conjugation buffer. For a 5 mer (MW 1500, 1.14 mg peptide was added to 10 mg BSA). This peptide solution was added to the pooled fractions containing maleimide-activated/biotinylated BSA. After 2 h incubation at room temperature, 100 ml cysteine solution was added to block the non-reacted maleimide groups. After 1 h, the reaction solution was dialysed 5 times with 1 ml PBS, in an ultrafiltration unit. The biotinylated conjugate was dissolved in PBS and aliquots stored at $-20°$ C.

2) Competitive ELISA of Biotinylated Peptide-BSA Conjugates on Anti-PSA mAb 2.1) Materials, Buffers and Method 2.1.1) Materials mAb 735 and 30H12
MaxiSorp™ plates (NUNC) for coating the antibody: ELISA plates
microtiter plates (NUNC) for peptide dilution: dilution plates
Biotinylated peptide-BSA conjugates prepared as above described
Extravidin alkaline phosphatase-avidin conjugate (SIGMA E2636)
p-nitrophenyl-phosphatase alkaline substrate (SIGMA 104-105)

2.1.2) Buffers

PBS pH 7.4
Blocking solution: 0.5% BSA in PBS
TBS
TBST: TBS containing 0.05% Tween 20
Extravidin alkaline phosphatase-avidin conjugate solution: 1/5000 in TBST
Alkaline phosphatase substrate solution; 1 tablet in 5 ml 50 mM $NaHCO_3$, 1 mM $MgCl_2$ solution, pH 9.6.
mixed competitor solution: 1 mM colominic acid with a peptide-BSA conjugate gradient in TBST 2.1.3) Method Maxisorp™ plate wells were coated with 100 µl mAb solution (25 µg/ml) for 2 h at room temperature. The control wells of the ELISA plates were only coated with the blocking solution. In parallel, the peptide-BSA conjugate dilution plates were blocked with 200 µl blocking solution for 2 h. The antibody coated wells and the control wells were blocked with 200 µl blocking solution for 1 h. In parallel the peptide-BSA conjugate dilution plates were washed 6 times with TBST and 120 µl TBST was added to the wells. An appropriate volume of peptide-BSA conjugate solution was added to the first well and the volume adjusted to 140 µl with TBST. The peptide-BSA conjugate in well one was diluted in the ratio 1/7 by taking 20 µl out of the first well and transferring into the second also to achieve the total volume of 140 µl. This was repeated for the remaining wells. The peptide-BSA conjugate dilutions for the control wells were done the same way. The blocked ELISA plates were washed 6 times with TBST and the peptide-BSA conjugate dilutions or 100 µl of the mixed competitor solution was added to the wells. After incubation for 1 h, the wells were washed 10 times with TBST and 100 µl of the alkaline phosphatase substrate solution was added to the wells. The plates were read out after 10 to 60 min using a microplate reader at 405 nm.

2.2) Results

The specificity of peptide p21 (SEQ ID NO: 1) was investigated in a competition ELISA using biotinylated p21-BSA conjugate and a randomized variant of p21 (p22) conjugate as a control. The results presented in Tables X and XI are expressed as percentage of binding by comparison with peptide p21 at the highest concentration (9.45 10-5 M) which corresponds to 100% binding.

TABLE X

Binding of p21 to mAb 735 in competitive ELISA

| | Peptide concentration (M) | | | | | | | | |
|---|---|---|---|---|---|---|---|---|---|
| | $9.45 \times 10^{-5}$ | $1.67 \times 10^{-5}$ | $2.94 \times 10^{-6}$ | $5.20 \times 10^{-7}$ | $9.27 \times 10^{-8}$ | $1.62 \times 10^{-9}$ | $2.86 \times 10^{-9}$ | $5.04 \times 10^{-10}$ | $8.89 \times 10^{-11}$ |
| Peptide + mAb 735 | 100 ± 11 | 93 ± 10 | 95 ± 1 | 91 ± 2 | 93 ± 9 | 56 ± 4 | 13 ± 1 | 2 ± 0 | 0 ± 0 |
| Peptide + colominic acid + mAb 735 | 43 ± 3 | 34 ± 3 | 23 ± 1 | 15 ± 3 | 5 ± 2 | 0 ± 1 | 0 ± 0 | 0 ± 0 | 0 ± 0 |
| Peptide + chondroitin sulfate C + mAb 735 | 96 ± 8 | 99 ± 4 | 99 ± 8 | 94 ± 7 | 92 ± 2 | 50 ± 1 | 11 ± 2 | 3 ± 0 | 2 ± 0 |
| Peptide + BSA | 3 ± 1 | 1 ± 0 | 0 ± 0 | 0 ± 0 | 0 ± 0 | 0 ± 0 | 0 ± 0 | 0 ± 0 | 0 ± 0 |

TABLE XI

Binding of p22 to mAb 735 in competitive ELISA

| | Peptide concentration (M) | | | | | | | | |
|---|---|---|---|---|---|---|---|---|---|
| | $9.45 \cdot 10^{-5}$ | $1.67 \cdot 10^{-5}$ | $2.94 \cdot 10^{-6}$ | $5.20 \cdot 10^{-7}$ | $9.27 \cdot 10^{-8}$ | $1.62 \cdot 10^{-9}$ | $2.86 \cdot 10^{-9}$ | $5.04 \cdot 10^{-10}$ | $8.89 \cdot 10^{-11}$ |
| Peptide + mAb 735 | 32 ± 1 | 9 ± 0 | 1 ± 0 | 0 ± 0 | 0 ± 0 | 0 ± 0 | 0 ± 0 | 0 ± 0 | 0 ± 0 |
| Peptide + colominic acid + mAb 735 | 27 ± 0 | 5 ± 0 | 0 ± 0 | 0 ± 0 | 0 ± 0 | 0 ± 0 | 0 ± 0 | 0 ± 0 | 0 ± 0 |
| Peptide + chondroitin sulfate C + mAb 735 | 29 ± 0 | 8 ± 1 | 3 ± 1 | 2 ± 0 | 2 ± 1 | 2 ± 0 | 2 ± 0 | 2 ± 0 | 2 ± 0 |
| Peptide + BSA | 3 ± 1 | 1 ± 1 | 0 ± 0 | 0 ± 0 | 0 ± 0 | 0 ± 0 | 0 ± 0 | 0 ± 0 | 0 ± 0 |

Table X shows a clear inhibition of p21 binding in the presence of colominic acid. By comparison, chondroitin sulfate C had no influence on the binding of peptide B. Table XI shows no binding to mAb 735 for the randomized variant of p21 conjugate (p22); no differences were observed when colominic acid or chondroitic sulfate C were present. These results lead to the conclusion that sequence SEQ ID NO: 1 (peptide p21) binds specifically to mAb 735 in a concentration-dependent manner.

3) ELISA with Peptide-BSA Conjugate

The specificity of the cyclic peptides was investigated in an ELISA assay using plates coated with 30H12 antibody, following the protocol as described above for the competitive ELISA, with the exception that the competitor was omitted. The results presented in FIG. 12A demonstrate that the cyclic peptides bind to the antibody in an antigen-specific manner. Peptides p65 and p66 exhibiting the highest binding were chosen for further studies.

4) Competitive Binding to PSA-NCAM Expressing Cells

The specificity of p65 and p66 peptides was tested in a competition assay using anti-PSA antibodies and PSA-NCAM expressing cells. Pre-incubation of the 30H12 monoclonal antibody with 0.1 mM of either p65 or p66 peptide prevented its binding to PSA-NCAM expressing cells (FIG. 12D versus 12B). The binding specificity was examined in greater detail by testing peptide recognition by another anti-PSA monoclonal antibody (MenB). The results presented in FIG. 12C demonstrate that p65 and p66 peptides bind only to 30H12; pre-incubation of the peptides with MenB did not prevent recognition of PSA-NCAM (FIG. 12 C). Thus, p65 and p66 mimotopes appear to be specific for a unique (idiotypic) determinant.

EXAMPLE 8

Analysis of PSA Mimetic Peptides Bioactivity

1) Materials and Methods
   1.1) Animals
   GFP transgenic mice have been previously described in Hadjantonakis et al. (Biotechnol., 2002, 2, 11-), and all analysis was performed on Swiss background. NCAM knock out mice (NCAM −/−) have been previously described in Cremer et al., precited.
   1.2) Dorsal Root Ganglions (DRG) Explant Culture
   E13.5 DRGs were dissected out from mice embryos in HBSS medium and seeded on glass coverslips coated with polylysine or with peptides linked to BSA. Explants were cultured in the presence or the absence of the peptides under soluble form (40 µM) in two ml of neurobasal medium (DMEM/Ham's F12, 3:1 (V/V), GIBCO, buffered with 20 mM Hepes), supplemented as described in Faivre-Sarrailh et al., J. Cell. Sci., 1999, 18, 3015-3027 and Chazal et al., J.Neurosci., 2000, 20, 1446-1457.
   1.3) Subventricular Zone (SVZ) Explant Culture.
   Cultures of SVZ explants were performed as described in Chazal et al., precited. Briefly, 1-day-old mice were killed by rapid decapitation. Brains were dissected out and sectionned by Vibratome (Leica). The SVZ from the lateral wall of the anterior lateral ventricle horn was dissected out in HBSS medium (LIFE TECHNOLOGIES) and cut into 200-300 µm diameter explants. The explants were mixed with Matrigel (BECKTON DICKINSON) and cultured in four-well dishes. After polymerisation, the gel was overlaid with 400 µl of serum-free medium containing B-27 supplement (LIFE TECHNOLOGIES), in the presence or the absence of 40 µM of peptides (p65, p66, reverse p65, p21 or p22) and 70 U of Endo N per milliliter.
   1.4) Immunohistochemistry
   Fixed DRGs (Dorsal Root ganglia) explants and sections were incubated at 4° C. respectively 2 hr with an anti-neurofilament (SMI-31, dilution 1:800, STERNBERGER MONOCLONALS) and overnight with an anti-PSA antibody (dilution 1:200, Rougon et al, J. Cell. Biol., 1986, 103, 2429-2437). Revelation was performed by 1 hr incubation with the corresponding fluorescent-labeled secondary antibody (Goat anti-mouse IgM or IgG conjugated with texas red, IMMUNOTECH)
   1.5) Cell Migration Distance (SVZ Explants) and Neuronal Outgrowth (DRG Explants).
   After 48 h in culture, explants were examining directly (SVZ) or after overnight fixation with a 4% paraformaldehyde solution in PBS and immunostaining (DRGs). Observation was done using 2, 5×, 5×, 10× and 32× objectives (Axiovert 35M, ZEISS). Images were collected with a video camera (Cool View, PHOTONIC SCIENCE) and analysed using image-processing software (Visiolab1000, BIOCOM). Mean migration distance (calculated on five different experiments, including at least five explants per condition) or mean length of the longest neurite (calculated on two different experiments, including at least eight explants per condition), was the distance in micrometers between the explant edge and the border of the cell migration front. Four measurements were performed for each explant. The significance of the differences between the control and the different experimental conditions was calculated by Student's t test.
   1.6) Transplantation
   100 µm diameter explants of 1-day-old GFP mice SVZ were incubated fifteen minutes in DMEM supplemented with 10% fetal bovine serum in presence of 0.01 M of p65 or reverse peptide and stereotaxically grafted (0.5 µl) into six weeks old mice SVZ as described in Lois and Alvarez-Buylla (Science, 1994, 264, 1145-1148). Three or four days after the graft, animals were perfused intracardiacally with a 4% paraformaldehyde solution in PBS. Brains were dissected out, postfixed, cryoprotected, and freezed in isopentane. Sagittal serial sections (12 µm) were cut with a Leica microtome and immunostained as described above. GFP cells arriving in the olfactory bulb after three days were observed using UV fluorescence with a 40× objective (Axioscope, ZEISS) and counted on two different experiments (four animals per condition). The significance of the difference between the two conditions was calvalated by Student's t test.

1.7) Intravitreal Injections and Retinal Whole Mount.

Injections were performed as described in Monnier et al. (Developmental Biology, 2001, 229, 1-14). Briefly, a 2×2 cm window was cut into the shell over E3 chick embryos. One µl of Fast green with 10 mM of p65 or reverse peptide was injected into the right eye vitreous body using a capillary. After a five-days incubation at 37° C., (E8) retinae were dissected, spread onto nitrocellulose filters (MILIPORE), and fixed with 4% paraformaldehyde solution in PBS. Two small DiI (1,1'-dioctadecyl-3,3,3',3'-tetramethylindocarbocyanine perchlorate) crystals were applied dorsally to the optic fissure. Retinae were stored in the dark at 37° C. for 10 days until the dye reached the axonal growth cones in the fissure, mounted in glycerol:PBS (9:1, v:v) and analysed using confocal microscopy.

Figure 1:
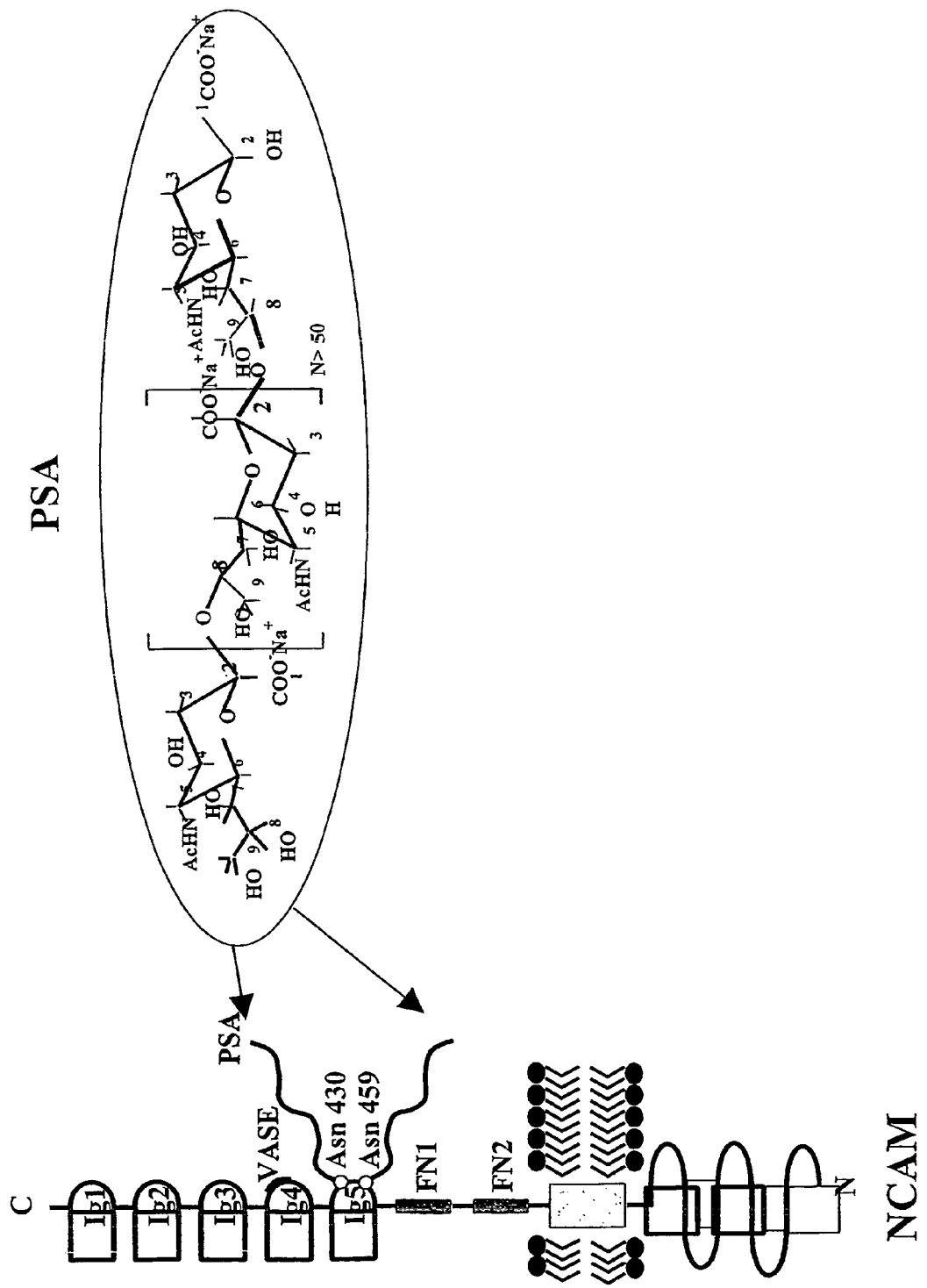
FIG. 1 illustrates PSA-NCAM structure.
Figure 2:
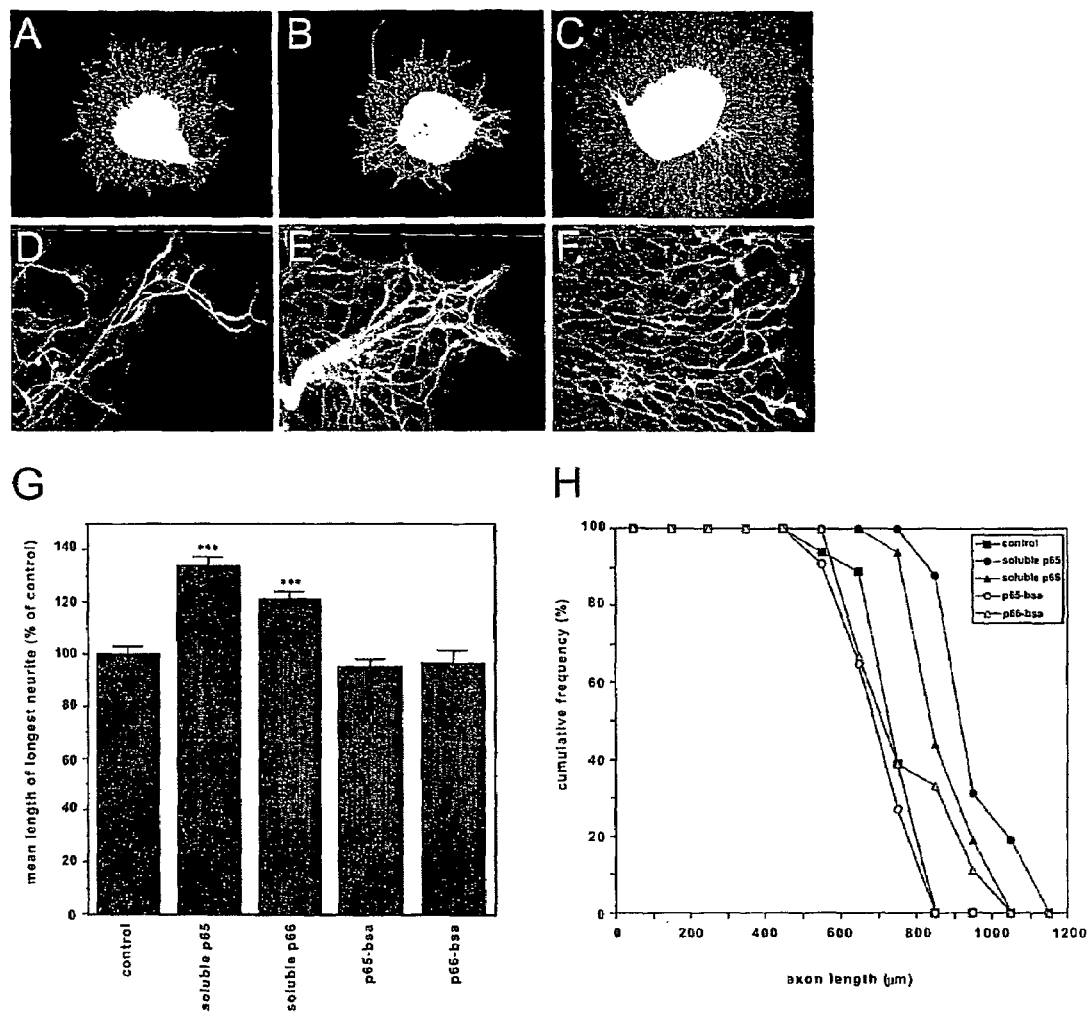
FIG. 2 illustrates the effect of PSA mimetic peptides p65 and p66, on neurite outgrowth in vitro: mouse dorsal root ganglion explants (E13,5) were cultured in absence (A, D) or presence of the p65 and p66 peptides coated on the microplates as BSA conjugate (B,E) or under soluble form (C,F).

2) Results 2.1) Effect of Psa Mimetic Peptides on Axonal Growth and Fasciculation In Vitro (FIG. 2)

Mouse dorsal root ganglion explants (E13.5) were cultured in the presence of p65 and p66 cyclic mimetic peptides, either in soluble form or coated on the microplates as BSA conjugates. Cells cultured in the absence of peptides or in the presence of reverse peptides (coated or in soluble form) were used as controls.

The effect of the peptides on neurite outgrowth and fasciculation was analysed qualitatively and quantitatively (FIG. 2 A to H).

p65 and p66, in a soluble form, induce a clear defasciculation of axon bundles (C versus A and F versus D) and a significant increase in axonal growth (C versus A) by comparison with the controls.

Interestingly, p65 and p66, in a coated form, induced an opposite effect on fasciculation (B versus A and E versus D) and no effect on neurite outgrowth.

These results were confirmed by quantitative analysis showing that p65 and p66, in soluble form, increased neurite outgrowth by 34% and 21% respectively, compared to the controls, whereas the same peptides in the coated form induce no significant increase on neurite outgrowth (FIGS. 2G and 2H).

These results demonstrate that PSA mimetic peptides are able to modulate axonal growth and fasciculation in vitro.

2.2) Effect of PSA Mimetic Peptides on Axonal Fasciculation and Guidance In Vivo (FIG. 3)

p65 and p66 were injected into chicken embryo eyes (E3) and the retina were observed at E9. The results presented in FIG. 3 show that the presence of PSA mimetic peptides during retina development induce axons guidance and fasciculation defects; axons leave their fascicle and run perpendicularly to it (arrowheads in D, G, E and H). By comparison, no defect in axon guidance and fasciculation is observed after injection of the control peptides.

These results demonstrate that PSA mimetic peptides are able to modulate axonal growth and guidance in vivo.

2.3) Effect of PSA Mimetic Peptides on Cell Migration In Vitro (FIGS. 4 to 7)

The effect of PSA mimetic peptides on cell migration in vitro was analysed on subventricular explants from 1-d-old normal mice (NCAM +/+), heterozygous (NCAM +/−) or knock out mice (NCAM −/−) cultured in Matrigel, in presence of the mimetic peptides (p65, p21, p66), different form of p65 peptide (cyclic, linear, linear and acetylated), the control peptides (reverse p65 and reverse p66 and p22) or endosialidase N. The results are illustrated in FIGS. 4 to 7.

FIG. 4 (A to I) show that the addition of p65 and p66 peptides to the culture increases the rate of migration of the neuronal precursors and a modification of their chain-like arrangement (C and F). These effects were not found with the reverse peptides (A and D) and were PSA-dependent since they were abolished by endo N treatment (B and E).

These results were confirmed by the quantitative analysis (G and H) demonstrating that p65 and p66 induce a significant increase in the rate of migration of the neuronal precursors (+40% and +26% respectively at 0.4 µM, compared with the control without peptide), whereas endo N decreases it (−21%, compared with the control without peptide).

Dose-response curve of p65 (1) shows that the optimal effect on cell migration is observed starting from and above 0.4 µM peptide.

FIG. 5 show that cyclisation of p65 is a prerequisite to p65 promoting effect since the corresponding amino acid sequences in a linear form, either N-acetylated or not, are unable to stimulate cell migration.

FIG. 6 show that p65 effect is dependant upon PSA expression since a significant reduction of the precursor migration was observed in the NCAM −/− mice by comparison to the NCAM +/−mice, in the presence of reverse peptide or p65 peptide; the effect were comparable in endo N treated NCAM +/−mice and NCAM +/− mice and the p65 did not reverse the impaired migration in the NCAM −/− mice.

FIG. 7 show that p65 induce a significant increase in the rate of migration of the neuronal precursors, compared to the corresponding control peptide transverse p65).

By contrast, p21 induces a significant decrease in the rate of migration of the neuronal precursors, compared to the corresponding control peptide (p22 peptide); the decrease is comparable to that observed in the endo N treated cells.

These results demonstrate that the mimetic peptides are able to stimulate (p65) or inhibit (p21) cell migration in a PSA-dependant manner.

2.4) Effect of PSA Mimetic Peptides on Cell Migration in vivo (FIG. 8)

The effect of PSA mimetic peptides on cell migration in vivo was analysed by grafting tissue and evaluating migration of SVZ cells. Small pieces of SVZ tissue (100 µm diameter) from 1-day-old GFP mice were grafted in the SVZ area of adult mice, in the presence of p65, p65 reverse peptide or in the absence of peptide. The results are illustrated in FIG. 8.

FIG. 8 show that the presence of p65 peptide increases significantly the number of GFP positive cells migrating to the olfactory bulb (via the Rostral Migration Stream or RMS), by comparison with the control. This effect was observed as early as 3 days post-engraftment (FIG. 8E). These results were confirmed by the quantitative analysis showing that the number of GFP positive cells present in the olfactory bulb 3 days after the graft is increased 17 times in the presence of p65, by comparison with the control (FIG. 8G).

These effects were PSA-dependent since they were abolished in NCAM knock-out mice.

These results demonstrate that the mimetic peptides are able to increase the migration of PSA positive cells.

EXAMPLE 9

Analysis of Functional Recovery from Spinal Cord Injury after Injection of PSA Mimetic Peptides 1) Material and Methods 1.1) Spinal Cord Surgery and Peptide Delivery Male Swiss-CD1 mice (8-10 week-old) were anesthetized with a mixture of ketamine and xylazine. The spinal cord had been exposed by making a midline incision of the skin, and by retracting the paravertebral muscles. A laminectomy was performed at the T7-T8 level and the spinal cord exposed. Using iridectomy scissors, a bilateral dorsal hemisection, transecting left and right dorsal finiculus, the dorsal horns, but sparing most parts of the ventral fimiculus, was performed, resulting in a complete transection of the dorsomedial main Cortico Spinal Tract (CST). For the series of mice receiving the peptides a Surgicoll pledget saturated with 10 µl of either p65 or reverse p65 (10 µM) peptides was applied over the transection site and covered with petroleum jelly to prevent diffusion. All inside muscle layer were sutured using fine thread. Skin was sutured using surgical staples. Following surgery, 1 ml of saline was administrated subcutaneously to prevent dehydratation, and the mice were placed under a heating lamp until they had recovered fully from the narcosis. The mice were then returned to their home cage and received a daily subcutaneous injection of antibiotic Baitryl™ to prevent infection. Manual bladder evacuation was made until recovery of complete autonomic bladder function.

1.2) Functional Testing (FIG. 9)

Functional evaluation of the animals was performed at day (D) D1, D4, D7, D14, D21, D28, D35, during the first week following the spinal cord lesion and then on a weekly basis until D35, by two different observers blinded to group identity. Locomotor recovery was evaluated using the BBB test (Basso, Beattie and Bresnahan test; Basso et al., Restor. Neurol. Neurosci, 2002, 5, 189-218). The scale ranges from 0 (no observable hindlimb movement) to 21 (normal gait) and can be subdivided into three ranges. Scores from 0 to 7 correspond to a low recovery (movements of joints, no weight-support, no paw placement). Scores from 8 to 13 can be related to an intermediate recovery (paw placement, fore-limb-hindlimb coordination). Scores from 14 to 21 can be related to a very good recovery. Finally on the last day of test (D35), mice were subjected to the rotarod test to assess fine motor coordination.

1.3) Histology (FIG. 9)

At D5, lesioned animals which received either p65 (n=3) or reversed p65 (n=3) were transcardiacally perfused. Spinal cords were sectioned in the sagittal plane at 20 µm intervals in blocks of 10 mm length at the lesion site. To examine lesion extent, Nissl staining was performed in series of 1-in-6 sections in all animals. Series of 1-in-3 sections were stained with the MenB anti-PSA (mouse IgM) and/or anti-GFAP (mouse IgG) antibodies. Bound antibodies were revealed by the appropriate fluorescently labelled secondary antibodies.

2) Results

After severed lesions, brain and spinal axons do not advance through the adult CNS. Instead, these fibres are trapped at the site of damage and remain disconnected from synaptic targets, leading to profound and persistent deficits in many clinical cases. Spinal cord injury (SCI) is the clearest example of a condition in which axonal disconnection leads to significant disability despite minimal neuronal death.

Thus, the effect of the p65 PSA mimetic peptides (and its reverse counterpart, taken as control) on functional recovery from spinal cord injury was analyzed in mice.

2.1) Improved Locomotor Recovery after Spinal Cord Injury in Mice which Received p65 Peptide at the Site of Lesion The results presented in FIG. 10 (A and B) demonstrate that PSA mimetic peptide treatment is correlated with functional recovery after midthoracic dorsal hemisection injury. More precisely, recovery was assessed using a standardized open-field measure of locomotor function after spinal cord injury, the BBB score. In this scale, 21 is normal function and 0 is bilateral total paralysis of the hind limbs. All mice had scores of 0 at D1 post injury. The p65-treated mice gradually recovered partial function over a 45 day observation period (FIG. 10A). The scores of p65-treated mice were significantly higher than p65-reverse controls starting from D14 post-injury and throughout the following time-points. Considering the time-period (14 days) when this improvement is observed it is compatible with some long-distance growth of CST fibers extending from the lesion site to the lumbar motor pool. Local sprouting in the lumbar cord as well as rearrangements of other descending tracts, such as the rubrospinal system, or of distal intrinsic spinal cord circuitry might also contribute. Regardless of mechanism, the locomotor recovery in the p65-treated mice was significantly greater than in control animals. The p65 beneficial effect on recovery was further assessed by a rotarod test performed at D35 (FIG. 10B).

2.2) Decrease of Reactive Gliosis at D5

To assess the effect of the peptide, quantification of the Glial Fibrillary acidic Protein (GFAP) expression as an index of reactive gliosis, was undertaken in a subset of animals taken D5 following surgery. These animals were selected in a blinded manner for quantification. 3 p65 (10 slices per animal) and 3 p65-reverse (10 slices per animal) animals were analyzed. Double-labelling was performed with MenB anti-PSA antibody. Quantification was also performed in a blinded manner.

A significant difference between p65 treated and p65-reverse animals was observed (FIGS. 11A and B), demonstrating that p65-treatment reduced reactive gliosis by 40% compared with the reverse p65-treatment, possibly by preventing migration inside the scar or by inhibiting other processes involved such as action of inflammatory cytokines. In any case these results supported the fact that functional recovery was better in p65-treated mice.

The invention claimed is:

1. A cyclic peptide comprising SEQ ID NO:18, wherein the side chain of the cysteine residue at position 1 of SEQ ID NO:18 is covalently attached to the side chain residue of the cysteine at position 11 via a disulfide bond.

2. The cyclic peptide of claim 1, which consists of SEQ ID NO:18.

3. A composition comprising the cyclic peptide of claim 1 and a pharmaceutically acceptable carrier.

4. A method of preparing a pharmaceutical composition, comprising combining the cyclic peptide of claim 1 and a pharmaceutically acceptable carrier to form the pharmaceutical composition.

* * * * *